(12) United States Patent
Shiah et al.

(10) Patent No.: US 9,610,246 B2
(45) Date of Patent: Apr. 4, 2017

(54) SUSTAINED DRUG DELIVERY IMPLANT

(71) Applicant: ALLERGAN, INC., Irvine, CA (US)

(72) Inventors: Jane-Guo Shiah, Irvine, CA (US); Chetan Pujara, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/218,324

(22) Filed: Mar. 18, 2014

(65) Prior Publication Data

US 2014/0234390 A1    Aug. 21, 2014

Related U.S. Application Data

(63) Continuation of application No. 14/181,250, filed on Feb. 14, 2014, now abandoned.

(60) Provisional application No. 61/765,554, filed on Feb. 15, 2013.

(51) Int. Cl.
*A61K 9/00* (2006.01)
*A61K 31/498* (2006.01)
*A61F 9/00* (2006.01)

(52) U.S. Cl.
CPC .......... *A61K 9/0051* (2013.01); *A61F 9/0017* (2013.01); *A61K 31/498* (2013.01); *A61F 2210/0004* (2013.01); *Y10S 514/912* (2013.01); *Y10S 514/913* (2013.01); *Y10S 514/953* (2013.01); *Y10S 514/954* (2013.01); *Y10S 514/956* (2013.01)

(58) Field of Classification Search
None
See application file for complete search history.

(56) References Cited

U.S. PATENT DOCUMENTS

| | | |
|---|---|---|
| 3,845,770 A | 11/1974 | Theeuwes et al. |
| 3,916,899 A | 11/1975 | Theeuwes et al. |
| 4,008,864 A | 2/1977 | Torphammar et al. |
| 4,014,335 A | 3/1977 | Arnold |
| 4,052,505 A | 10/1977 | Higuchi et al. |
| 4,057,619 A | 11/1977 | Higuchi et al. |
| 4,063,064 A | 12/1977 | Saunders et al. |
| 4,088,864 A | 5/1978 | Theeuwes et al. |
| 4,144,317 A | 3/1979 | Higuchi et al. |
| 4,158,005 A | 6/1979 | Bodor et al. |

(Continued)

FOREIGN PATENT DOCUMENTS

| | | |
|---|---|---|
| CA | 1333770 | 1/1995 |
| CA | 2294714 | 1/1999 |

(Continued)

OTHER PUBLICATIONS

Acheampong, Andrew, Distribution of Brimonidine Into Anterior and Posterior Tissues of Monkey, Rabbit, and Rat Eyes, The American Society for Pharmacology and Experimental Therapeutics, Jan. 4, 2002, 421-429, 30 (4).

(Continued)

*Primary Examiner* — Isaac Shomer
(74) *Attorney, Agent, or Firm* — Laura L. Wine

(57) ABSTRACT

Biocompatible intraocular implants may include a brimonidine free base and a biodegradable polymer associated with the brimonidine free base to facilitate the release of the brimonidine free base into an eye with the polymer matrix lasts a period of time of not more than twice the drug release duration, but more than the drug release duration.

3 Claims, 7 Drawing Sheets

(56) References Cited

U.S. PATENT DOCUMENTS

| | | | |
|---|---|---|---|
| 4,186,184 A | 1/1980 | Zaffaroni |
| 4,190,642 A | 2/1980 | Gale et al. |
| 4,200,098 A | 4/1980 | Ayer et al. |
| 4,281,654 A | 8/1981 | Shell et al. |
| 4,285,987 A | 8/1981 | Ayer et al. |
| 4,303,637 A | 12/1981 | Shell et al. |
| 4,304,765 A | 12/1981 | Shell et al. |
| 4,327,725 A | 5/1982 | Cortese |
| 4,396,625 A | 8/1983 | Yamamori et al. |
| 4,425,346 A | 1/1984 | Horlington et al. |
| 4,474,451 A | 10/1984 | Mizokami |
| 4,478,818 A | 10/1984 | Shell et al. |
| 4,494,274 A | 1/1985 | Thurlow |
| 4,521,210 A | 6/1985 | Wong |
| 4,599,353 A | 7/1986 | Bito |
| 4,649,151 A | 3/1987 | Dougherty et al. |
| 4,656,186 A | 4/1987 | Bommer et al. |
| 4,668,506 A | 5/1987 | Bawa |
| 4,675,338 A | 6/1987 | Bommer et al. |
| 4,693,885 A | 9/1987 | Bommer et al. |
| 4,712,500 A | 12/1987 | Montandon |
| 4,853,224 A | 8/1989 | Wong |
| 4,863,457 A | 9/1989 | Lee |
| 4,865,846 A | 9/1989 | Kaufman |
| 4,866,168 A | 9/1989 | Dougherty et al. |
| 4,932,934 A | 6/1990 | Dougherty et al. |
| 4,935,498 A | 6/1990 | Sessler et al. |
| 4,959,217 A | 9/1990 | Sanders et al. |
| 4,968,715 A | 11/1990 | Dougherty et al. |
| 4,981,871 A | 1/1991 | Abelson |
| 4,997,652 A | 3/1991 | Wong |
| 5,002,962 A | 3/1991 | Pandey et al. |
| 5,017,579 A | 5/1991 | Gubin et al. |
| 5,019,400 A | 5/1991 | Gombotz et al. |
| 5,028,621 A | 7/1991 | Dougherty et al. |
| 5,034,413 A | 7/1991 | Chan et al. |
| 5,075,115 A | 12/1991 | Brine |
| 5,089,509 A | 2/1992 | Chandraratna |
| 5,093,349 A | 3/1992 | Pandey et al. |
| 5,100,431 A | 3/1992 | Buster et al. |
| 5,164,188 A | 11/1992 | Wong |
| 5,169,638 A | 12/1992 | Dennis et al. |
| 5,171,741 A | 12/1992 | Dougherty |
| 5,173,504 A | 12/1992 | Dougherty |
| 5,190,966 A | 3/1993 | Dougherty et al. |
| 5,198,460 A | 3/1993 | Pandey et al. |
| 5,268,178 A | 12/1993 | Calhoun et al. |
| 5,300,114 A | 4/1994 | Gwon et al. |
| 5,314,905 A | 5/1994 | Pandey et al. |
| 5,356,629 A | 10/1994 | Sander et al. |
| 5,378,475 A | 1/1995 | Smith |
| 5,385,887 A | 1/1995 | Yim et al. |
| 5,438,071 A | 8/1995 | Clauss et al. |
| 5,443,505 A | 8/1995 | Wong et al. |
| 5,459,159 A | 10/1995 | Pandey et al. |
| 5,466,233 A | 11/1995 | Weiner et al. |
| 5,501,856 A | 3/1996 | Ohtori et al. |
| 5,504,074 A | 4/1996 | D'Amato et al. |
| 5,587,371 A | 12/1996 | Sessler et al. |
| 5,587,479 A | 12/1996 | Makovec et al. |
| 5,597,897 A | 1/1997 | Ron et al. |
| 5,632,984 A | 5/1997 | Wong et al. |
| 5,655,832 A | 8/1997 | Pelka et al. |
| 5,656,297 A | 8/1997 | Berstein et al. |
| 5,688,819 A | 11/1997 | Woodward |
| 5,707,643 A | 1/1998 | Ogura |
| 5,766,242 A | 6/1998 | Wong et al. |
| 5,770,589 A | 6/1998 | Billson et al. |
| 5,776,699 A | 7/1998 | Klein et al. |
| 5,798,349 A | 8/1998 | Levy et al. |
| 5,824,072 A | 10/1998 | Wong |
| 5,824,074 A | 10/1998 | Koch |
| 5,856,329 A | 1/1999 | Wheeler |
| 5,869,079 A | 2/1999 | Wong et al. |
| 5,877,207 A | 3/1999 | Klein et al. |
| 5,882,682 A | 3/1999 | Rork et al. |
| 5,906,920 A | 5/1999 | Evans et al. |
| 5,913,884 A | 6/1999 | Trauner et al. |
| 5,919,970 A | 7/1999 | Song et al. |
| 5,922,773 A | 7/1999 | Lipton et al. |
| 5,958,954 A | 9/1999 | Klein et al. |
| 6,051,576 A | 4/2000 | Ashton et al. |
| 6,066,675 A | 5/2000 | Wen et al. |
| 6,074,661 A | 6/2000 | Olejnik et al. |
| 6,194,415 B1 | 2/2001 | Wheeler |
| 6,217,869 B1 | 4/2001 | Meyer et al. |
| 6,217,895 B1 | 4/2001 | Guo et al. |
| 6,225,303 B1 | 5/2001 | Miller et al. |
| 6,248,741 B1 | 6/2001 | Wheeler |
| 6,258,319 B1 | 7/2001 | Hearst et al. |
| 6,270,492 B1 | 8/2001 | Sinofsky |
| 6,270,749 B1 | 8/2001 | Blumenkranz et al. |
| 6,271,220 B1 | 8/2001 | Garst et al. |
| 6,274,614 B1 | 8/2001 | Richter et al. |
| 6,290,713 B1 | 9/2001 | Russell |
| 6,294,361 B1 | 9/2001 | Horowitz et al. |
| 6,306,426 B1 | 10/2001 | Olejnik et al. |
| 6,309,669 B1 | 10/2001 | Setterstrom et al. |
| 6,317,616 B1 | 11/2001 | Glossop |
| 6,319,273 B1 | 11/2001 | Chen et al. |
| 6,331,313 B1 | 12/2001 | Wong et al. |
| 6,357,568 B1 | 3/2002 | Chen |
| 6,369,116 B1 | 4/2002 | Wong et al. |
| 6,403,649 B1 | 6/2002 | Woodward |
| 6,410,045 B1 | 6/2002 | Schultz |
| 6,447,796 B1 | 9/2002 | Vook et al. |
| 6,455,062 B1 | 9/2002 | Olejnik et al. |
| 6,465,464 B2 | 10/2002 | Wheeler et al. |
| 6,482,854 B1 | 11/2002 | Lipton et al. |
| 6,497,729 B1 | 12/2002 | Moussy et al. |
| 6,537,568 B2 | 3/2003 | Olejnik et al. |
| 6,548,078 B2 | 4/2003 | Guo et al. |
| 6,565,871 B2 | 5/2003 | Roser et al. |
| 6,573,280 B2 | 6/2003 | Dreyer |
| 6,595,945 B2 | 7/2003 | Brown |
| 6,692,759 B1 | 2/2004 | Wong et al. |
| 6,699,493 B2 | 3/2004 | Wong |
| 6,713,081 B2 | 3/2004 | Robinson et al. |
| 6,726,918 B1 | 4/2004 | Wong et al. |
| 6,765,012 B2 | 7/2004 | Andrews et al. |
| 7,268,126 B2 | 9/2007 | Liu et al. |
| 7,368,126 B2 | 5/2008 | Chen et al. |
| 7,589,057 B2 | 9/2009 | Chang et al. |
| 7,714,024 B2 | 5/2010 | Hughes |
| 7,931,909 B2 | 4/2011 | Hughes |
| 8,293,210 B2 | 10/2012 | Huang et al. |
| 8,293,741 B2 | 10/2012 | Burke et al. |
| 8,506,986 B2 | 8/2013 | Huang et al. |
| 2001/0023363 A1 | 9/2001 | Harth et al. |
| 2001/0049369 A1 | 12/2001 | Jablonski |
| 2002/0010202 A1 | 1/2002 | Garst |
| 2002/0032201 A1 | 3/2002 | Olejnik |
| 2002/0040015 A1 | 4/2002 | Miller et al. |
| 2002/0094998 A1 | 7/2002 | Burke et al. |
| 2002/0111357 A1 | 8/2002 | Wheeler et al. |
| 2003/0018078 A1 | 1/2003 | Woodward et al. |
| 2003/0069286 A1 | 4/2003 | Chen et al. |
| 2003/0069560 A1 | 4/2003 | Adamis et al. |
| 2003/0095995 A1 | 5/2003 | Wong et al. |
| 2003/0157178 A1 | 8/2003 | Chen et al. |
| 2003/0185873 A1 | 10/2003 | Chasin et al. |
| 2003/0199478 A1 | 10/2003 | Andrews et al. |
| 2003/0225152 A1 | 12/2003 | Andrews et al. |
| 2004/0001889 A1 | 1/2004 | Chen |
| 2004/0013704 A1 | 1/2004 | Kabra et al. |
| 2004/0054374 A1 | 3/2004 | Weber et al. |
| 2004/0151753 A1 | 8/2004 | Chen et al. |
| 2004/0170665 A1 | 9/2004 | Donovan |
| 2004/0198829 A1 | 10/2004 | Sponsel et al. |
| 2004/0208910 A1 | 10/2004 | Ashton et al. |
| 2004/0266776 A1 | 12/2004 | Gil |
| 2005/0043246 A1 | 2/2005 | Mitra |
| 2005/0154399 A1 | 7/2005 | Weber et al. |
| 2005/0244458 A1 | 11/2005 | Huang et al. |

(56) References Cited

U.S. PATENT DOCUMENTS

| | | | |
|---|---|---|---|
| 2005/0244463 | A1 | 11/2005 | Huang |
| 2005/0244467 | A1 | 11/2005 | Nivaggioli et al. |
| 2005/0244476 | A1* | 11/2005 | Burke et al. ............. 424/427 |
| 2005/0244479 | A1 | 11/2005 | Huang et al. |
| 2005/0244506 | A1 | 11/2005 | Burke et al. |
| 2006/0233860 | A1 | 10/2006 | Chang |
| 2008/0112922 | A1 | 5/2008 | Hughes et al. |
| 2008/0118547 | A1 | 5/2008 | Jackson et al. |
| 2008/0118548 | A1 | 5/2008 | Jackson et al. |
| 2008/0118549 | A1 | 5/2008 | Huang et al. |
| 2008/0131372 | A1 | 6/2008 | Huang et al. |
| 2008/0131485 | A1 | 6/2008 | Huang et al. |
| 2008/0139652 | A1 | 6/2008 | Sakai et al. |
| 2008/0260832 | A1 | 10/2008 | Huang et al. |
| 2008/0286334 | A1 | 11/2008 | Shiah et al. |
| 2008/0299178 | A1 | 12/2008 | Huang et al. |
| 2010/0124565 | A1* | 5/2010 | Spada et al. ............. 424/428 |
| 2011/0251201 | A1 | 10/2011 | Huang et al. |
| 2012/0276184 | A1* | 11/2012 | Ghebremeskel ..... A61K 9/0051 424/426 |

FOREIGN PATENT DOCUMENTS

| | | |
|---|---|---|
| EP | 0364417 | 4/1990 |
| EP | 0488401 | 6/1992 |
| EP | 0430539 | 10/1994 |
| EP | 0992244 | 4/2000 |
| WO | 95-13765 | 5/1995 |
| WO | 96-38174 | 12/1996 |
| WO | 01-30323 | 5/2001 |
| WO | 01-58240 | 8/2001 |
| WO | 01-70230 | 9/2001 |
| WO | 02-02076 | 1/2002 |
| WO | 02-36162 | 5/2002 |
| WO | 02-43785 | 6/2002 |
| WO | 03-048190 | 6/2003 |
| WO | 03-077952 | 9/2003 |
| WO | 03-099795 | 12/2003 |
| WO | 2004-066979 | 8/2004 |
| WO | 2005-107705 | 11/2005 |
| WO | 2005-110362 | 11/2005 |
| WO | 2005-110367 | 11/2005 |
| WO | 2005-110368 | 11/2005 |
| WO | 2006-122165 | 11/2006 |
| WO | 2007-150018 | 12/2007 |
| WO | 2008-070402 | 6/2008 |
| WO | 2010-056598 | 5/2010 |

OTHER PUBLICATIONS

Ahmed, Farid A.K.M. et al, Neuroprotective Effect α2 Agonist (Brimonidine) on Adult Rat Retinal Ganglion Cells After Increased Intraocular Pressure, Brain Research, 2001, 133-139, 913.
Allergan, Alphagan Product Information, Product Sheet, 2005, 1-10.
Allergan, Inc., Tazorac Product Information Sheet, 2004, 1-8.
Alm, Albert et al, Lactate Transport Through the Blood-Retinal and the Blood-Brain Barrier in Rats, Ophthalmic Res., 1985, 181-184, 17.
AlphaganP, Physician's Desk Reference, Product Information, 54th Edition, 493-494, 2001.
Anderson, Lynne et al, An Injectable Sustained Release Fertility Control System, Contraception, 1976, 375-384, 13.
Atluri, Harisha et al, Mechanism of a Model Dipeptide Transport Across Blood-Ocular Barriers Following Systemic Administration, Experimental Eye Research, 2004, 815-822, 78.
Aukunuru, Jithan et al, Expression of Multidrug Resistance-Associated Protein (MRP) in Human Retinal Pigment Epithelial Cells and Its Interaction with BAPSG, a Novel Aldose Reductase Inhibitor, Pharmaceutical Research, 2001, 565-572, 18(5).
Baker, Richard, Controlled Release of Biologically Active Agent, A Wiley, 1987, 73-75, Interscience Publication.
Bartlett, J.D. et al, Contrast Sensitivity Improvements in Brimonidine-Treated Primary Open-Angle Glaucoma Patients Suggest a Neuroprotective Mechanism, ARVO Meeting, 2002, 1 Page, Biosis.
Basu, Sujit et al, Proton-Driven Dipeptide Uptake in Primary Cultured Rabbit Conjunctival Epithelial Cells, Invest. Ophthalmol. Vis. Sci., 1998, 2365-2373, 39.
Berger, Urs et al, Distribution of Peptide Transporter PEPT2 mRNA in the Rat Nervous System, Anat. Embryol, 1999, 439-449, 199.
Bergersen, L. et al, Cellular and Subcellular Expression of Monocarboxylate Transporters in the Pigment Epithelium and Retina of the Rat, Neuroscience, 1999, 319-331, 90(1).
Bito, L. Z, Prostaglandins, Other Eicosanoids, and Their derivatives as Potential Antiglaucoma Agents, Glaucoma: Applied Pharmacology, 1984, 477-505, 20.
Bito, LZ, Biological Protection with Prostanoids, CRC Press, Inc., 1985, 231-252, 1, Cohen, M. M., ed., Boca Raton, Fla.
Bito, LZ, Prostaglandins, Old Concepts and New Perspectives, Archives of Ophthalmology, 1987, 1036-1039, 105.
Blazynski, Christine, The Accumulation of [3H]phenylisopropyl Adenosine ([3H]PIA) and [3H]adenosine Into Rabbit Retinal Neurons is Inhibited by Nitrobenzylthioinosine (NBI), Neuroscience Letters, 1991, 1-4, 121.
Bodor, Nicholas et al, A Comparison of Intraocular Pressure Elevating Activity of Loteprednoletabonate and Dexamethasone in Rabbits, Current Eye Research, 1992, 525-530, 11.
Brecha, Nicholas et al, Expression of GAT-1, a High-Affinity Gamma-Aminobutyric Acid Plasma Membrane Transporter in the Rat Retina, The Journal of Comparative Neurology, 1994, 602-611, 345.
Brubaker, Richard, Mechanism of Action of Bimatoprost (LumiganTM), Surv Ophthalmol, 2001, S347-S351, 45-Suppl 4.
Busse, Dagmar et al, Tyrosine Kinase Inhibitors: Rationale, Mechanisms of Action, and Implications for Drug Resistance, Semin Oncol, 2001, 47-55, 28-Suppl 16.
CAS Registry Record from STN-59803-98-4, 1984, 1 Page.
Chancy, Christy et al, Expression and Differential Polarization of the Reduced-Folate Transporter-1 and the Folate Receptor α in Mammalian Retinal Pigment Epithelium, The Journal of Biological Chemistry, 2000, 20676-20684, 275(27).
Charles, Jean-Bernard et al, Use of Bioerodible Polymers Impregnated with Mitomycin in Glaucoma Filtration Surgery in Rabbits, Ophthalmology, Apr. 1991, 503-508, 98-4.
Chen, June et al, LumiganR: A Novel Drug for Glaucoma Therapy, Optom in Pract., Jun. 12, 2002, 95-102, 3.
Cheng, Cheng-Kuo et al., Intravitreal Sustained-Release Dexamethasone Device in the Treatment of Experimental Uveites, Investigative Ophthalmology & Visual Science, 1995, 442-453, 96 (2).
Chiang, Chiao-Hsi et al, Pharmacokinetics and Intraocular Pressure Lowering Effect of Timolol Preparations in Rabbit Eyes, Journal of Ocular Pharmacology and Therapeutics, 1996, 471-480, 12(4).
Cleland, Jeffrey et al, Development of Poly-(D,L-lactide-coglycolide) Microsphere Formulations Containing Recombinant Human Vascular Endothelial Growth Factor to Promote Local Angiogenesis, Journal of Controlled Release, 2001, 13-24, 72.
Clive, Migdal, Lumigan(R): A New Ocular Hypotensive Agent for Achieving Target Intraocular Pressure, ACTA Ophthalmol Scand Scientific Abstracts, 2002, 457, 80-4.
Coleman, Anne et al, A 3-Month Randomized Controlled Trial of Bimatoprost (LUMIGAN) Versus Combined Timolol and Dorzolamide (Cosopt) in Patients with Glaucoma or Ocular Hypertension, Ophthalmology, 2003, 2362-8, 110-12.
Conti, B. et al, Biodegradable Microspheres for the Intravitreal Administration of Acyclovir In Vitro/In Vivo Evaluation, European Journal of Pharmaceutical Sciences, 1997, 287-293, 5.
Coquelet, P. et al, Successful Photodynamic Therapy Combined with Laser Photocoagulatio in Three Eyes With Classic Subfoveal Choroidal Neovascularisation Affecting Two Patients With Multifocal Choroiditis: Case Reports, Bull. Soc. Beige Ophthalmal, 2002, 69-73, 283.

(56) References Cited

OTHER PUBLICATIONS

Cunha-Vaz, Jose G., The Blood-Ocular Barriers: Past, Present, and Future, Documenta Ophthalmolgica, Advances in Ophthalmology, 1997, 149-157, 93.

De Jong, S.J. et al, New insights into the hydrolytic degradation of poly(lactic acid): participation of the alcohol terminus, Polymer, 2001, 2795-2802, 42.

De, T.K. et al., Brimonidine Formulation in Polyacrylic Acid Nanoparticles for Opthalmic Delivery, Jouranl of Microencapsulation, 2003, 361-374, 20 (3).

Di Colo, Giacomo, Controlled Drug Release From Implantable Matrices Based on Hydrophobic Polymers, Biomaterials, 1992, 850-856, 13(12).

Donello, John E., et al, alpa2-Adrenoceptor Agonists Inhibit Vitreal Glutamate and Aspartate Accumulation and Preserve Retinal Function after Transient Ischemia, The American Society for Pharmacology and Experimental Therapeutics, 2001, pp. 216-223, vol. 296, No. 1.

Duvvuri, Sridhar et al, Drug Delivery to the Retina: Challenges and Opportunities, Expert Opin Biol Ther, 2003, 45-56, 3(1).

Ocheltree, Scott et al, Preliminary Investigation Into the Expression of Proton-Coupled Oligopeptide Transporters in Neural Retina and Retinal Pigment Epithelium (RPE): Lack of Functional Activity in RPE Plasma Membranes, Pharmaceutical Research, Sep. 2003, 1364-1372, 20(9).

Enyedi, Laura et al, An Intravitreal Device Providing Sustained Release of Cyclosporins and Dexamethason, Current Eye Research, 1996, 549-557.

Epstein, David, Primary Open-Angle Glaucoma, Chandler and Grant's Glaucoma, 1986, 129-181.

Evans, D.W. et al, Contrast Sensitivity Improves After Brimonidine Therapy in Primary Open Angle Glaucoma: A Case for Neuroprotection, Br. J. Ophthalmol, 2003, 1463-1465, 87.

Fabbro, Doriano et al, Protein Tyrosine Kinase Inhibitors: New Treatment Modalities?, Current Opinion in Pharmacology, 2002, 374-381, 2.

Fotsis, Theodore et al, The Endogenous Oestrogen Metabolite 2-methoxyoestradiol inhibits Angiogeneses and Suppresses Tumour Growth, Current Opinion in Pharmacology, 1994, 368, 237.

Gandolfi, S.A. et al, Is There a Non IOP-Related Effect of Brimonidine on Visual Field Progression in Human Glaucoma?, Invest Ophthalmol Vis Sci, 2004, E-Abstract 2298, 45.

Gao, Bo et al, Localization of Organic Anion Transport Protein 2 in the Apical Region of Rat Retinal Pigment Epithelium, Invest Ophthalmol Vis Sci, 2002, 510-514, 43.

Gao, Hua et al, Up-Regulation of Brain-Derived Neurotrophic Factor Expressior by Brimonidine in Rat Retinal Ganglion Cells, Arch. Ophthalmol., 2002, 797-803, 120.

George, Ronald et al, Transport of N-Acetylaspartate Via Murine Sodium/Dicarboxylate Cotransporter NaDC3 and Expression of This Transporter and Aspartoacylase II in Ocular Tissues in Mouse, Biochimica et Biophysica Acta, 2004, 63-69, 1690.

Gerhart, D.Z. et al, Distribution of Monocarboxylate Transporters MCT1 and MCT2 in Rat Retina, Neuroscience, 1999, 367-375, 92(1).

Gherzi, Roberto et al, High Expression Levels of the "Erythroid/ Brian" Type Glucose Transporter (GLUT1) in the Basal Cells of Human Eye Conjunctiva and Oral Muscosa Reconstituted in Culture, Experimental Cell Research, 1991, 230-236, 195.

Gilman et al, The Pharamceutical Basis of Therapeutics, Goodman and Gilman's, 1990, 1447-1451, 8th Edition.

Goel, Sanjay et al, Tyrosine Kinase Inhibitors: A Clinical Perspective, Current Oncology Reports, 2002, 9-19, 4.

Greenwood, J., Characterization of a Rat Retinal Endothelial Cell Culture and the Expression of P-Glycoprotein in Brain and Retinal Endothelium in Vitro, Journal of Neuroimmunology, 1992, 123-132, 39.

Gu, Sumin et al, Characterization of an N-System Amino Acid Transporter Expressed in Retina and Its Involvement in Glutamine Transport, The Journal of Biological Chemistry, Jun. 2001, 24137-24144, 276(26).

Guenther, Lyn, Optimizing Treatment with Topical Tazarotene, Am. J. Clin. Dermotol, 2003, 197-202, 4-3.

Hainsworth, Dean et al, Sustained Release Intravitreal Dexamethasone, Journal of Ocular Pharmacology and Therapeutics, 1996, 57-63, 12-1.

Haluska, Paul et al, Receptor tyrosine kinase inhibitors, Current Opinion in Investigational Drugs, 2001, 280-286, 2-2.

Hamann, Steffen et al, Cotransport of H+, Lactate, and H2O in Porcine Retinal Pigment Epithelial Cells, Experimental Eye Research, 2003, 493-504, 76.

Han, Yong-Hae et al, Characterization of a Novel Cationic Drug Transporter in Human Retinal Pigment Epithelial Cells, Journal of Pharmacology and Experimental Therapeutics, 2001, 450-457, 296.

Han, Zhiqiang et al, Regulation of Aquaporin-4 Water Channels by Phorbol Ester-Dependent Protein Phosphorylation, The Journal of Biological Chemistry, 1998, 6001-6004, 273(11).

Hare, William et al, Efficacy and Safety of Memantine, an NMDA-Type Open-Channel Blocker, from Reduction of Retinal Injury associated with Experimental Glaucoma in Rat and Monkey, Sur Ophthalmol, 2001, S284-S289, 45-Suppl. 3.

Harik, Sami et al, Glucose Transporters Are Abundant in Cells With "Occluding" Junctions at the Blood-Eye Barriers, Proc. Natl. Acad. Sci., Jun. 1990, 4261-4264, 87.

Hashizoe, Mototane et al, Scleral Plugof Biodegradable Polymers for Controlled Drug Release in the Vitreous, Arch Ophthalmol, 1994, 1380-1384, 112.

Hasson, D. et al, Functional Protection of Rat Retina From Ischemic Injury by Brimonidine, Society for Neuroscience, Oct. 25-30, 1997, 72.4, 23(1).

Heller, J., Hydrogels in Medicine and Pharmacy, N.A. Peppes ed., 1987, 137-149.

Heller, Jorge, Biodegradable Polymers in Controlled Drug Delivery, Critical Reviews in Therapeutic Drug Carrier Systems, 1987, 39-90, 1 (1).

Herrero-Vanrell, Rocio et al, Biodegradable Microspheres for Vitreoretinal Drug Delivery, Advanced Drug Delivery, 2001, 5-16, 52.

Honda, Shigeru et al, Immunocytochemical Localization of Three Subtypes of GABA Transporter in Rat Retina, Molecular Brain Research, 1995, 319-325, 33.

Horibe, Yoshihide et al, Carrier-Mediated Transport of Monocarboxylate Drugs in the Pigmented Rabbit Conjunctiva, Invest Ophthalmol Vis Sci, 1998, 1436-1443, 39.

Horibe, Yoshihide et al, Kinetic Evidence for Na+-Glucose Co-Transport in the Pigmented Rabbit Conjunctiva, Current Eye Research, 1997, 1050-1055.

Horibe, Yoshihide et al, Polar Soluted Transport Across the Pigmented Rabbit Conjunctiva: Size Dependence and the Influence of 8-Bromo Cyclic Adenosine Monophosphate, Pharmaceutical Research, 1997, 1246-1251, 14(9).

Hosoya, Ken-Ichi et al, Contribution of Na+-glucose Cotransport tot he Short-Circuit Current in the Pigmented Rabbit Conjunctiva, Current Eye Research, 1996, 447-451, 15.

Hosoya, Ken-Ichi et al, MCT1-Mediated Transport of L-Lactic Acid at the Inner Blood-Retinal Barrier: A Possible Route for Delivery of Monocarboxylic Acid Drugs to the Retina, Pharmaceutical Research, Dec. 2001, 1669-1676, 18(12).

Hosoya, Ken-Ichi et al, Na+-Dependent L-Arginine Transport in the Pigmented Rabbit Conjunctiva, Exp Eye Res, 1997, 547-553, 65.

Hosoya, Ken-Ichi et al, Nucleoside Transport Mechanisms in the Pigmented Rabbit Conjunctiva, Invest Ophthalmol Vis Sci, 1998, 372-377, 39.

Hoyng, Philip et al, Pharmacological Therapy for Glaucoma, Drugs 2000, 2000, 411-434, 59 (3).

Hu, M. et al, Expression of GABA Transporter Subtypes (GAT1, GAT3) in the Developing Rabbit Retina, Acta Ophthalmol. Scand., 1999, 261-265, 77.

Hubbard, Stevan et al, Protein Tyrosine Kinase Structure and Function, Annu. Rev. Biochem., 2000, 373-98, 69.

(56) References Cited

OTHER PUBLICATIONS

Inoue, Kiyoshi et al, Cloning and Expression of a Bovine Glutamate Transporter, Molecular Brain Research, 1995, 343-348, 28.

Ito, Aki et al, Distribution of Organic Anion-Transporting Polypeptide 2 (oatp2) and oatp3 in the Rat Retina, Invest Ophthalmol Vis Sci, 2002, 858-863, 43.

Ito, Aki et al, Distribution of Rat Organic Anion Transporting Polypeptide-E (oatp-E) in the Rat Eye, Invest Ophthalmol Vis Sci, 2003, 4877-4884, 44.

Jackanicz, Theodore et al, Polyactic Acid as a Biodegradable Carrier for Contraceptive Steroids, Contraception, 1973, 227-235, 8-3.

Jampel, Henry et al, Glaucoma Filtration Surgery in Monkeys Using 5-Fluorouridine in Polyanhydride Disks, Arch Ophthalmol, Mar. 1990, 430-435, 108.

John Wiley, Encyclopedia of polymer science and Engineering, 1985, vol. 3.

Kennedy, Brian et al, P-Glycoprotein Expression in Human Retinal Pigment Epithelium, Molecular Vision, 2002, 422-430, 8.

Kenyon, Emily et al, Lactate Transport Mechanisms at Apical and Basolateral Membranes of Bovine Retinal Pigment Epithelium, Am J Physiol, 1994, C1561-C1578, 267.

Kim, In-Beom et al, Immunocytochemical Localization of Aquaporin 1 in the Rat Retina, Neuroscience Letters, 1998, 52-54, 244.

Kimura, Hideya et al, A New Vitreal Drug Delivery System Using an Implantable Biodegradable Polymeric Device, Invest Ophthalmol Vis Sci, 1994, 2815-2819, 35.

Knott, R.M. et al, A Model System for the Study of Human Retinal Angiogenesis: Activation of Monocytes and Endothelial Cells and the Association with the Expression of the Monocaroxylate Transporter Type 1 (MCT-1), Diabetologica, 1999, 870-877, 42.

Knott, R.M. et al, Regulation of Glucose Transporter (GLUT 3) and Aldose Reductase mRNA in Bovine Retinal Endothelial Cells and Retinal Pericytes in High Glucose and High Galactose Culture, Diabetologica, 1993, 808-812, 36.

Kochinke, F. et al, Biodegradable Drug Delivery System for Uveitis Treatment, Investigative Ophthalmology & Visual Science, Feb. 15, 1996, 186-B98, 37(3).

Kompella, Udaya Bhaskar et al, Possible Existence of Na+-Coupled Amino Acid Transport in the Pigmented Rabbit Conjuctiva, Life Sciences, 1995, 1427-1431, 57(15).

Kwak, Hyung Woo et al, Evaluation of the Retinal Toxicity and Pharmacokinetics of Dexamethasone After Intravitreal Injection, Arch. Ophthalmol, 1992, 259-66, 110.

Lai, Ronald et al, Alpha-2 Adrenoceptor Agonist Protects Retinal Function After Acute Retinal Ischemic Injury in the Rat, Vis Neurosci, 2002, 175-185, 19.

Lee, David et al, Glaucoma Filtration Surgery in Rabbits Using Bioerodible Polymers and 5-Fluorouacil, Ophthalmol, Dec. 1987, 1523-1530, 94-12.

Lee, David et al, The Use of Bioerodible Polymers and 5-Fluorouracils in Glaucoma Filtration Surgery, Ophthalmology & Visual Science, Nov. 1988, 1692-1697, 29-11.

Lee, Susan et al, Biodegradable Implants for Sustained Drug Release in the Eye, Pharm Res, 2010, 2043-2053, 27.

Lewis, Danny, Controlled Release of Bioactive Agents from Lactide/Glycolide Polymers, Biodegradable Polymers as Drug Delivery Systems, 1990, 1-35, 45.

Macular Degeneration Genetics, Oct. 31, 2006, http://macular-degeneration.emedtv.com/macular-degeneration/macular-degeneration-genetics.html, 1 Page.

Majumdar, Soumyajit et al, Mechanism of Ganciclovir Uptake by Rabbit Retina and Human Retinal Pigmented Epithelium Cell Line ARPE-19, Current Eye Research, 2004, 127-136, 29(2-3).

Mantych, Gregory et al, Characterization of Glucose Transporter Isoforms in the Adult and Developing Human Eye, Endocrinology, 1993, 600-607, 133(2).

Marks, R., Topical Tazarotene:Review and Re-Evaluation, Retinoids, 2001, 72-74, 17(3).

Maurice, David, Micropharmaceutics of the Eye, Ocular Inflammation Ther., 1983, 97-102, 1.

Mayo Clinic Com, Stargardt's Disease: Can It Be Treated?, May 27, 2008, 2 Pages.

Merck Manuals, Retinitis Pigmentosa, 2005, http://merck.com/mmpe/print/sec09/ch106/ch106h.html, printed May 27, 2008. 2 Pages.

Merkli, Alain et al, Use of Insoluble Biodegradable Polymers in Ophthalmic Systems for the Sustained Release of Drugs, European Journal of Pharmaceutics and Biopharmaceutics, 1995, 271-283, 41 (5).

Miller, Robert et al, Degradation Rats of Oral Resorbable Implants (Polyactates and Polyglycolates): Rate Modification with Changes in PLA/PGA Copolymer Ratios, J. Biomed Materials Res, 1977, 711-719, 11.

Miller, Thomas et al, Synthesis and Structure-Activity Profiles of A-Homoestranes, the Estratopones, J. Med. Chem., 1997, 3836-3841, 40.

Mondal, L.K. et al, The Efficacy of Topical Administration of Brimonidine to Reduce Ischaemia in the Very Early Stage of Diabetic Retinopathy in Good Controlled Type-2 Diabetes Mellitus, J India Med Assoc, 2004, 724-729, 102.

Newman, Hereditary Optic Neuropathis: From the Mitochondria to the Optic Nerve, American Journal of Ophthalmology, 2005, 517e1-517e8, 140(3).

Oculex, Oculex Announces Positive Clinical Results for Posurdex(r) the first biodegradable ocular implant, PR Newswire, Aug. 6, 2002, 1-2.

Olsen, Timothy et al, Human Scleral Permeability: Effects of Age, Cryotherapy, Transcleral Diode Laser, and Surgical Thinning, Invest. Ophthalmol. Vis. Sci., 1995, 1893-1903, 36.

Patil, Rajkumar et al, Expression of Aquaporins in the Rat Ocular Tissue, Exp Eye Res, 1997, 203-209, 64.

Peterson, Ward et al, Identification and Functional Characterization of a Dual GABA/Taurine Transporter in the Bullfrog Retinal Pigment Epithelium, J. Gen. Physiol., Dec. 1995, 1089-1122, 106.

Phillips, Calbert et al, Penetration of Timolol Eye Drops into Human Aqueous Humor: The First Hour, British Journal of Ophthalmology, 1985, 217-218, 69.

Phillips, Tania et al, Efficacy of 0.1% Tazarotene Cream for the treatment of Photodamage, Arch Dermatol, Nov. 2002, 1486-1493, 138(11).

Philp, Nancy et al, Monocarboxylate Transporter MCT1 is Located in the Apical Membrane and MCT3 in the Basal Membrane of Rat RPE, Am. J. Physiol., 1998, R1824-R1828, 43.

Philp, Nancy et al, Polarized Expression of Monocarboxylate Transporters in Human Retinal Pigment Epithelium and ARPE-19 Cells, Invest Ophthalmol Vis Sci, 2003, 1716-1721, 44.

Physician's Desk Reference for Ophthalmic Medicines, 30th Edition, 285-294, 2002.

Pignataro, Leonardo et al, Nonsynaptic Localization of the Excitatory Amino Acid Transporter 4 in Photoreceptors, Mol. Cell. Neurosci., 2005, 440-451, 28.

Pribluda, Victor et al, 2-Methoxyestradiol: An Endogenous Antiangionic and Antiproliferative Drug Candidate, Cancer and Metastasis Reviews, 2000, 173-179, 19.

Quigley, Harry et al, The Mechanism of Optic Nerve Damage in Experimental Acute Intraocular Pressure Elevation, Invest Ophthalmol. Vis. Sci., 1980, 505-517, 19.

Rajan, Prasanna et al, Expression of the Extraneuronal Monoamine Transporter in RPE and Neural Retina, Current Eye Research, 2000, 195-204, 20(3).

Rao et al, Intraocular Inflammation and Uveitis, Basic and Clinical Science Course; Intraocular Inflammation and Uveitis, 1998-1999, 57-80; 102-103; 152-156, Section 9; Part 2.

Rauen, T., Diversity of Glutamate Transporter Expression and Function in the Mammalian Retina, Amino Acids, 2000, 53-62, 19.

Renfro, Lisa et al, Ocular Effects of Topical and Systemic Steroids, Dermatologic Clinics, 1992, 505-512, 10.

Roff, W.J. et al, Fibres, Films, Plastics and Rubbers, A Handbook of Common Polymers, 1971, 7 Pages, 1.

Rowe, Raymond et al, Aliphatic Polyesters, Handbook of Pharmaceutical Excipients, Nov. 2003, 19-21, 4th Edition.

(56) References Cited

OTHER PUBLICATIONS

Ruiz, Maria et al, Cloning, Expression, and Localization of a Mouse Retinal γ-Aminobutyric Acid Transporter, Invest Ophthalmol Vis Sci, 1994, 4039-4048, 35.
Saba, Pratik et al, Existence of a p-Glycoprotein Drug Efflux Pump in Cultured Rabbit Conjunctival Epithelial Cells, Invest Ophthalmol Vis Sci, 1998, 1221-1226, 39.
Schmidt-Erfurth, Ursula et al, Management of Neovascular Age-Related Macular Degeneration, Progress in Retinal and Eye Research, 2007, 437-451, 26.
Schonfeld, David, Lumigan Found Effective in Early Phase 3, Ocul. Surg. News, Mar. 1, 2001, 35, 19(5)1.
Schuettauf, Frank et al, Effects of anti-glaucoma Medications on Ganglion Cell Survival: the DBA/2J Mouse Model, Vision Res., 2002, 2333-2337, 42(20).
Schumacher, Guido et al, The Physiological Estrogen Metabolite 2-Methoxyestradiol Reduced Tumor Growth and Induces Apoptosis in Human Solid Tumors, J Cancer Res Clin Oncol, 2001, 405-410, 127.
Schwartz, Bernard, The Response of Ocular Pressure to Corticosteroids, Ophthamol. Clin. North Am., 1966, 929-989, 6.
Shi, Xiao-Ping et al, Active Sodium and Chloride Transport Across the Isolated Rabbit Conjunctiva, Current Eye Research, 1995, 927-935, 14.
Siebold et al., Esterified Prostaglandin Shows 'Potent' Promise, Ocular Surgery News, Feb. 1, 1989, pp. 3, 59, 1.
Skalka, Harold et al, Effect of Corticosteroids on Cataract Formation, Arch. Ophthalmol, 1980, 1773-1777, 98.
Smith, Thomas et al, Sustained-Release Subconjunctival 5-Fluorouracil, Ophthalmic Surgery and Laser, Sep. 1996, 763-767, 27-9.
Starr, Michael, Further Studies on the Effects of Prostagladin on Intraocular Pressure in the Rabbit, Exp. Eye Res., 1971, 170-177, 11.
Steuer, Heiko et al, Functional Characterization and Comparison of the Outer Blood-Retina Barrier and the Blood-Brain Barrier, Invest Ophthalmol Vis Sci, 2005, 1047-1053, 46.
Tazarotene, Drugs Future, 208-209-2003.
Tenckhoff, Solveig et al, Diversity of Aquaporin mRNA Expressed by Rat and Human Retinas, NeuroReport, 2005, 53-56, 16.
To, Chi Ho et al, The Saturation Characteristics of Glucose Transport in Bovine Retinal Pigment Epithelium, Eye Science, 1998, 126-129, 14(3).
Tornquist, P. et al, Carrier-Mediated Transport of Amino Acids Through the Blood-Retinal and the Blood-Brain Barriers*, Graefe's Arch Clin Exp Ophthalmol, 1986, 21-25, 224.
Tracy, M.A. et al, Factors Affecting the Degradation Rate of Poly(actide-co-glycolide) Microspheres in Vivo and in Vitro, Biomaterials, 1999, 1057-1062, 20.
Tsukamoto, Hidetoshi et al, Isoforms of Glucose Transporter in the Iris-Cillary Body, Jpn J Ophthalmol, 1995, 242-247, 39.
Ueda, Hideo et al, Functional Characterization of Organic Cation Drug Transport in the Pigmented Rabbit Conjunctiva, Invest Ophthalmol Vis Sci, 2000, 870-876, 41.
United States Pharmacopeia, The National Formulary, USP23, 1995, 1790-1798, 18.
Vijayasarathy, Camasamudram et al., Identification and Characterization of Two Mature Isoforms of Retinoschisin in Murine Retina, Biochemical and Biophysical Research Communications, 2006, 99-105, 349, US.
Walters et al, Expression, transport properties, and chromosomal location of organic anion transporter subtype 3, Am J Physiol Gastrointest Liver Physiol, 2000, G1188-G1200, 279.
Watanabe, Takashi et al, GLUT2 Expression in the Rat Retina: Localization at the Apical Endsof Muller Cells, Brain Research, 1994, 128-134, 655.
Watson, Peter et al, A Six-month, Randomized, Double-masked Study Comparing Latanoprost with Timolol in Open-Angle Glaucoma and Ocular Hypertension, Ophthalmology, 1996, 126-137, 103.
Wheeler, L.A. et al, Alpha-2adrenergic Receptor Agonists Are Neuroprotective in Experimental Models of Glaucoma, Eur J Ophthalmol, 2001, S30-S35, 11(Suppl 2).
Wheeler, Larry et al, Role of Alpha-2 Adrenergic Receptors in Neuroprotection and Glaucoma, Surv Ophthalmol, May 2001, S290-S294, vol. 45, Supplement 3.
Wheeler, Larry, Experimental Study of Agents with Potential Neuroprotective Properties, Acta Ophthalmol Scand, 1999, 27-28, 77.
Williams, Evans et al, Nucleoside Transport Sites in a Cultured Human Retinal Cell Line Established by SV-40 T Antigen Gene, Current Eye Research, 1994, 109-118, 13.
Woldemussie, Elizabeth et al, Neuroprotection Effects of Memantine in Different Retinal Injury Models of Glaucoma, J Glaucoma, 2002, 474-480, 11(6).
Woldemussie, Elizabeth, Neuroprotection of Retinal Ganglion Cells in Experimental Models of Glaucoma, Minerva Ophthalmol, 2000, 71-78, 42(2).
Woodward, David et al, AGN 192024 (LumiganR): A Synthetic Prostamide Analog that Lowers Primate Intraocular Pressure by Virtue of Its Inherent Pharmacological Activity, ARVO, 2002, 1 page (Abstract), 43.
Woodward, David et al, Pharmacology of Bimatoprost (LumiganTM), Survey of Ophthalmology, May 2001, S337-S345, vol. 45.
Yasukawa, T. et al., Biodegradable Scleral Plugs for Vitreoretinal Drug Delivery, Advanced Drug Delivery Reviews, 2001, 25-36, 52, US.
Zhao, Jing-Wei et al, Expression of GABA Transporters on Bullfrog Retinal Muller Cells, GLIA, 2000, 104-117, 31.
Zhao, Jing-Wei et al, Glutamate Transporter EAAC1 is Expressed on Muller Cells of Lower Vertebrate Retinas, Journal of Neuroscience Research, 2001, 89-95, 66.
Zhou, Tianhong et al, Development of a Multiple-Drug Delivery Implant for Intraocular Management of Proliferative Vitreoretinopathy, Journal of Controlled Release, 1998, 281-295, 55.

\* cited by examiner

| Formulation | Day 0 | Day 1 | 1 Week | 1 Month | 3 Month | 6 Month |
|---|---|---|---|---|---|---|
| CE 1 | | | | | | |
| CE 2 | | | | | | |
| CE 3 | | | | | | |
| CE 4 | | | | | | |
| EX 1 | | | | | | (Disintegraded) |
| EX 2 | | | | | | (Disintegraded) |
| EX 3 | | | | | | (Disintegraded) |
| EX 4 | | | | (Disintegraded) | | |

FIG. 3

SUSTAINED DRUG DELIVERY IMPLANT

CROSS-REFERENCE TO RELATED APPLICATIONS

This application is a continuation of copending U.S. patent application Ser. No. 14/181,250 filed on Feb. 14, 2014, which claims the benefit of U.S. Provisional Application No. 61/765,554 filed on Feb. 15, 2013, the entire content of both applications are incorporated herein by reference.

BACKGROUND

Field

The disclosure of the present application generally relates to drug delivery implants, and more specifically, drug delivery implants used to treat ocular conditions.

Description of the Related Art

Diabetic retinopathy is the leading cause of blindness among adults aged 20 to 74 years. It is estimated that 75,000 new cases of macular edema, 65,000 cases of proliferative retinopathy, and 12,000 to 24,000 new cases of blindness arise each year. Retinitis pigmentosa (RP) is a heterogeneous group of inherited neurodegenerative retinal diseases that cause the death of photoreceptor cells (rods and cones) that eventually leads to blindness. Glaucoma is a multifactorial optic neuropathy resulting from loss of retinal ganglion cells, corresponding atrophy of the optic nerve, and loss of visual function, which is manifested predominantly by visual field loss and decreased visual acuity and color vision. Geographic atrophy ("GA") is one of 2 forms of the advanced stage of Age-Related Macular Degeneration ("AMD"). The advanced stage of AMD refers to that stage in which visual acuity loss can occur from AMD. Retinal detachments are a significant cause of ocular morbidity. There are 3 types of retinal detachment: rhegmatogenous, tractional, and exudative.

Brimonidine (5-bromo-6-(2-imidazolidinylideneamino)quinoxaline) is an alpha-2-selective adrenergic receptor agonist effective for treating open-angle glaucoma by decreasing aqueous humor production and increasing uveoscleral outflow. Brimonidine tartrate ophthalmic solution 0.2% (marketed as ALPHAGAN®) was approved by the US Food and Drug Administration (FDA) in September 1996 and in Europe in March 1997 (United Kingdom). Brimonidine tartrate ophthalmic solution with Purite® 0.15% and 0.1% (marketed as ALPHAGAN® P) was approved by the FDA in March 2001 and August 2005, respectively. These formulations are currently indicated for lowering IOP in patients with open-angle glaucoma (OAG) and ocular hypertension (OHT).

A neuroprotective effect of brimonidine tartrate has been shown in animal models of optic nerve crush, moderate ocular hypertension, pressure-induced ischemia, and vascular ischemia. The neuroprotective effect of topical applications of brimonidine tartrate has also been explored clinically in patients with glaucoma, age-related macular degeneration, retinitis pigmentosa, diabetic retinopathy, and acute non-arteritic anterior ischemic optic neuropathy. However, certain limitations exist with the use of brimonidine tartrate in intraocular implants.

For example, because of the size of the brimonidine tartrate molecule, the amount of drug that can be loaded into an implant may be limited. Also, the hydrophilic nature of brimonidine tartrate may limit the ability of the drug's use in sustained release formulations.

SUMMARY

Accordingly, an embodiment provides an intraocular implant for the treatment of a posterior ocular condition in a human patient including a biodegradable polymer matrix including at least one biodegradable polymer and a brimonidine free base agent, wherein the implant can be configured to deliver the brimonidine free base agent to the vitreous of an eye of a patient suffering from a posterior ocular condition for a brimonidine free base agent delivery duration of up to six months and wherein the biodegradable polymer matrix is configured to completely or almost completely degrade, once placed into the vitreous of the eye, within a period of time of about two times the brimonidine free base agent delivery duration or less. In some embodiments, the brimonidine free base agent is present in the implant in an amount of about 50% by weight of the implant, based on the total weight of the implant. In some embodiments, the implant can have a rod shape, and the rod shape can have a rod diameter of about 350 μm and a rod length of about 6 mm. According to other embodiments, the brimonidine free base agent is dispersed within the biodegradable polymer matrix. In some embodiments, the at least one biodegradable polymer includes poly(D,L-lactide-co-glycolide) and poly(D,L-lactide). In some embodiments, the biodegradable polymer matrix includes at least one polymer selected from the group consisting of acid-end capped poly(D,L-lactide-co-glycolide) and acid-end capped poly(D,L-lactide). In some embodiments, the brimonidine free base agent delivery duration is in the range of about 1 month to about 6 months.

These and other embodiments are described in greater detail below.

BRIEF DESCRIPTION OF THE FIGURES

These and other features will now be described with reference to the drawings summarized below. These drawings and the associated description are provided to illustrate one or more embodiments and not to limit the scope of the invention.

FIG. 3 shows implants images when incubating comparative example and example Formulations in PBS (pH 7.4, 0.01 M) at 37° C.

DETAILED DESCRIPTION

Figure 1:
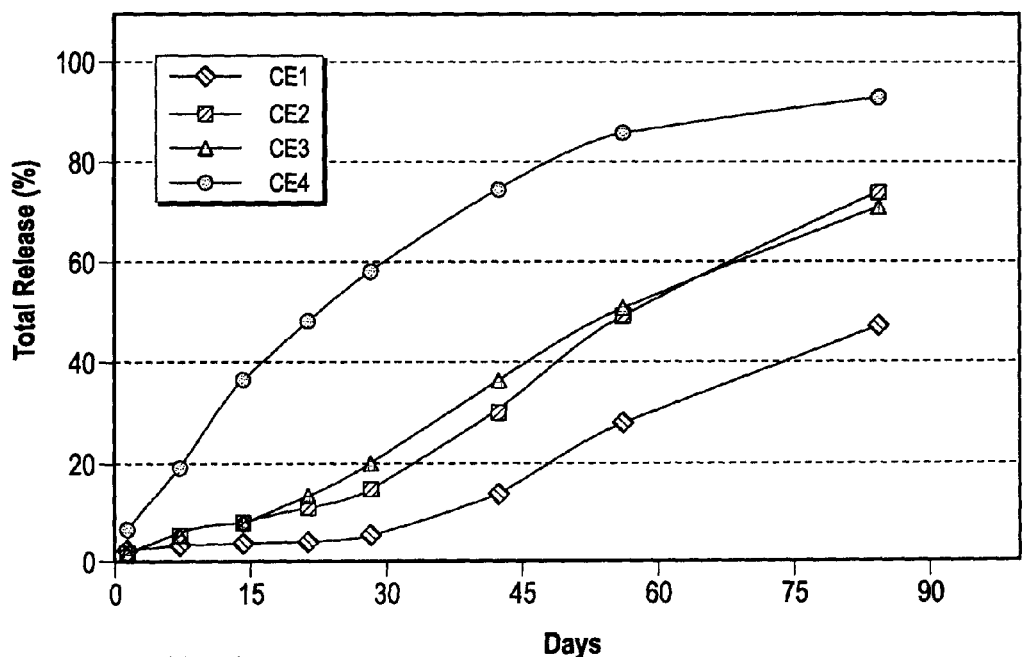
FIG. 1 illustrates brimonidine tartrate implant formulation drug release profiles in 0.01 M PBS with a pH of 7.4 at 37 C, according to comparative example formulations.

In general terms, an embodiment relates to brimonidine free base sustained delivery for back-of-the-eye therapeutic applications. In some embodiments, the brimonidine free base is formulated into an implant with one or more polymers in a polymer matrix, the polymers selected in order to give a target sustained delivery of the brimonidine free base and/or a target degradation of the one or more polymers. According to some embodiments, formulations of brimonidine free base and biodegradable polymer or polymers are created such that that the polymer matrix will be degraded within a period of not more than twice the brimonidine free base release duration, but more than the brimonidine free base release duration. According to some embodiments, the brimonidine free base drug delivery system exhibits a target drug delivery duration of one to six months and a target matrix degradation time of two to twelve months.

Embodiments herein disclose new drug delivery systems, and methods of making and using such systems, for extended or sustained drug release into an eye, for example, to achieve one or more desired therapeutic effects. The drug delivery systems can be in the form of implants or implant elements that can be placed in an eye. The systems and methods disclosed in some embodiments herein can provide for extended release time of one or more therapeutic agent or agents. Thus, for example, a patient who has received such an implant in their eye can receive a therapeutic amount of an agent for a long or extended time period without requiring additional administrations of the agent. According to some embodiments an implant may also only remain within the eye of a patient for a targeted or limited amount of time before it degrades completely or nearly completely. By limiting the amount of time a foreign object, such as an implant is in a patient's eye or vitreous, a patient's comfort is optimized and their risk for infection or other complications is minimized. Also, complications that may arise from an implant colliding with the cornea or other part of the eye in the dynamic fluid of the vitreous can be avoided.

As used herein, an "intraocular implant" refers to a device or elements that is structured, sized, or otherwise configured to be placed in an eye. Intraocular implants are generally biocompatible with physiological conditions of an eye. Intraocular implants may be placed in an eye without disrupting vision of the eye.

As used herein, "therapeutic component" refers to a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in the eye.

As used herein, an "ocular condition" is a disease ailment or condition which affects or involves the eye or one of the parts or regions of the eye. The eye can include the eyeball and the tissues and fluids that constitute the eyeball, the periocular muscles (such as the oblique and rectus muscles) and the portion of the optic nerve which is within or adjacent the eyeball.

An "anterior ocular condition" is a disease, ailment, or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition can affect or involve the conjunctiva, the cornea, the anterior chamber, the iris, the posterior chamber (located behind the retina, but in front of the posterior wall of the lens capsule), the lens or the lens capsule and blood vessels and nerve which vascularize or innervate an anterior ocular region or site.

A "posterior ocular condition" is a disease, ailment or condition which primarily affects or involves a posterior ocular region or site such as choroid or sclera (in a position posterior to a plane through the posterior wall of the lens capsule), vitreous, vitreous chamber, retina, optic nerve or optic disc, and blood vessels and nerves that vascularize or innervate a posterior ocular region or site.

Thus a posterior ocular condition can include a disease, ailment or condition such as, but not limited to, acute mascular neuroretinopathy; Behcet's disease; geographic atrophy; choroidal neovascularization; diabetic uvetis; histoplasmosis; infections, such as fungal, bacterial, or viral-caused infections; macular degeneration, such as acute macular degeneration, non-exudative age related macular degeneration and exudative age related macular degeneration; edema, such as macular edema, cystoids macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; or posterior ocular conditions caused by or influenced by a photodynamic therapy, photocoagulation, radiation retinotherapy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (e.g. neuroprotection).

The terms "biodegradable polymer" or "bioerodible polymer" refer to a polymer or polymers which degrade in vivo, and wherein erosion of the polymer or polymers over time occurs concurrent with and/or subsequent to the release of a therapeutic agent. A biodegradable polymer may be a homopolymer, a copolymer, or a polymer comprising more than two polymeric units. In some embodiments, a "biodegradable polymer" may include a mixture of two or more homopolymers or copolymers.

The terms "treat", "treating", or "treatment" as used herein, refer to reduction or resolution or prevention of an ocular condition, ocular injury or damage, or to promote healing of injured or damaged ocular tissue.

The term "therapeutically effective amount" as used herein, refers to the level or amount of therapeutic agent needed to treat an ocular condition, or reduce or prevent ocular injury or damage.

Those skilled in the art will appreciate the meaning of various terms of degree used herein. For example, as used herein in the context of referring to an amount (e.g., "about 6%"), the term "about" represents an amount close to and including the stated amount that still performs a desired function or achieves a desired result, e.g. "about 6%" can include 6% and amounts close to 6% that still perform a desired function or achieve a desired result. For example, the term "about" can refer to an amount that is within less than 10% of, within less than 5% of, within less that 0.1% of, or within less than 0.01% of the stated amount.

Intraocular implants can include a therapeutic component and a drug release control component or components. The therapeutic agent can comprise, or consist essentially of an alpha-2 adrenergic receptor agonist. The alpha-2 adrenergic receptor agonist may be an agonist or agent that selectively activates alpha-2 adrenergic receptors, for example by binding to an alpha-2 adrenergic receptor, relative to other types of adrenergic receptors, such as alpha-1 adrenergic receptors. The selective activation can be achieved under different conditions, such as conditions associated with the eye of a human patient.

The alpha-2 adrenergic receptor agonist of the implant is typically an agent that selectively activates alpha-2 adrenergic receptors relative to alpha-2 adrenergic receptors. In certain implants, the alpha-2 adrenergic receptor agonist selectively activates a subtype of the alpha-2 adrenergic receptors. For example, the agonist may selectively activate one or more of the alpha-2a, the alpha-2b, or the alpha-2c receptors, under certain conditions, such as physiological conditions. Under other conditions, the agonist of the implant may not be selective for alpha-2 adrenergic receptor subtypes. The agonist may activate the receptors by binding to the receptors, or by any other mechanism.

According to some embodiments, the alpha-2 receptor antagonist used is brimonidine. Brimonidine is a quinoxaline derivative having the structure:

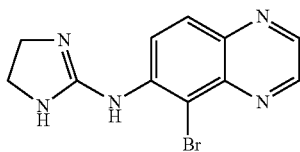 [SMILES: Brc1c(NC2=NCCN2)ccc2nccnc12]

Brimonidine, an organic base, is publicly available as brimonidine free base. Brimonidine free base is generally hydrophobic.

In some embodiments, the alpha-2 adrenergic receptor antagonist may be a pharmaceutically acceptable acid addition salt of brimonidine. One such salt can be brimonidine tartrate (AGN 190342-F, 5-bromo-6-(2-imidazolidinylideneamino) quinoxaline tartrate). Both brimonidine free base and brimonidine tartrate are chemically stable and have melting points higher than 200° C.

Thus, an intraocular implant can comprise, consist of, or consist essentially of a therapeutic agent such as an alpha-2 adrenergic receptor agonist such as a brimonidine salt alone (such as brimonidine tartrate), a brimonidine free base alone, or mixtures thereof.

The use of brimonidine free base in solid implant formulations has several advantages over brimonidine tartrate, such as the lower solubility of brimonidine free base lowers potential drug burst effect, and the free base drug equivalent dose per implant can be higher under the same weight. Thus, according to some embodiments, no brimonidine tartrate is included in an intraocular implant. According to some embodiment, the only therapeutic agent used in an intraocular implant is brimonidine free base.

The alpha-2 adrenergic receptor agonist may be in a particulate or powder form and entrapped by the biodegradable polymer matrix. According to an embodiment, the alpha-2 adrenergic receptor agonist is a brimonidine free base having a D90 particle size of less than about 20 μm. According to another embodiment, the alpha-2 adrenergic receptor agonist is a brimonidine free base having a D90 particle size of less than about 10 μm. According to another embodiment, the alpha-2 adrenergic receptor agonist is a brimonidine free base having a D90 particle size in the range of about 10 μm to about 20 μm.

According to some embodiments, implants can be formulated with particles of the brimonidine free base agent dispersed within the bioerodible polymer matrix. According to some embodiments, the implants can be monolithic, having the therapeutic agent homogenously distributed through the biodegradable polymer matrix, or encapsulated, where a reservoir of active agent is encapsulated by the polymeric matrix. In some embodiments, the therapeutic agent may be distributed in a non-homogeneous pattern in the biodegradable polymer matrix. For example, in an embodiment, an implant may include a first portion that has a greater concentration of the therapeutic agent (such as brimonidine free base) relative to a second portion of the implant.

The alpha-2 adrenergic receptor agonist can be present in an implant in an amount in the range of about 20% to about 70% by weight of the implant, based on the total weight of the implant. In some embodiments, the alpha-2 adrenergic receptor agonist can be present in an implant in an amount in the range of about 40% to about 60% by weight of the implant, based on the total weight of the implant. In an embodiment, the alpha-2 adrenergic receptor agonist can be present in an implant in an amount of about 40% by weight of the implant, based on the total weight of the implant. In another embodiment, the alpha-2 adrenergic receptor agonist can be present in an implant in an amount of about 50% by weight of the implant, based on the total weight of the implant. In an example embodiment, brimonidine free base can be present in an implant in an amount of about 50% by weight of the implant, about 55% by weight of the implant, about 60% by weight of the implant, or about 70% by weight of the implant, based on the total weight of the implant.

Suitable polymeric materials or compositions for use in the implant can include those materials which are compatible with the eye so as to cause no substantial interference with the functioning or physiology of the eye. Such materials can be at least partially or fully biodegradable.

Examples of suitable polymeric materials for the polymer matrix include polyesters. For example, polymers of D-lactic acid, L-lactic acid, racemic lactic acid, glycolic acid, polycaprolactone, and combinations thereof may be used for the polymer matrix. In some embodiments, a polyester, if used, may be a homopolymer, a copolymer, or a mixture thereof.

In some implants, copolymers of glycolic acid and lactic acid are used, where the rate of biodegradation can be controlled, in part, by the ratio of glycolic acid to lactic acid. The mol percentage (% mol) of polylactic acid in the polylactic acid polyglycolic acid (PLGA) copolymer can be between 15 mol % and about 85 mol %. In some embodiments, the mol percentage of polylactic acid in the (PLGA) copolymer is between about 35 mol % and about 65 mol %. In some embodiments, a PLGA copolymer with 50 mol % polylactic acid and 50 mol % polyglycolic acid can be used in the polymer matrix.

The polymers making up the polymer matrix may also be selected based on their molecular weight. Different molecular weights of the same or different polymeric compositions may be included in the implant to modulate the release profile. In some embodiments, the release profile of the therapeutic agent and the degradation of the polymer may be affected by the molecular weight of one or more polymers in the polymer matrix. In some embodiments, the molecular weight of one or more poly (D,L-lactide) components may be advantageously selected to control the release of the therapeutic agent and the degradation of the polymer. According to some embodiments, the average molecular weight of a polymer, such as poly (D,L-lactide), may be "low." According to some embodiments, the average molecular weight of a polymer, such as poly (D,L-lactide), may be "medium." According to some embodiments, only low molecular weight poly(D,L-lactide) is included in a polymer matrix in an intraocular implant. According to some embodiments, high molecular weight (Mw) poly(D,L-lactide)s are not present in the biodegradable polymer matrix or they are only present in a negligible amount (about 0.1% by weight of an implant, based on the total weight of the implant). By limiting the amount of high molecular weight poly(D,L-lactide) present in an implant, the matrix degradation duration may be shortened.

Some example polymers that may be used alone or in combination to form the polymer matrix include those listed in TABLE A below, the data sheets of the commercially available polymers are incorporated by reference, in their entirety:

TABLE A

| Trade Name of Commercially Available Polymer (From EVONIK) | Polymer | Intrinsic Viscosity (dL/g) | Molecular Weight (low, medium, high) |
|---|---|---|---|
| RG502S | 50:50 poly (D, L-lactide-co-glycolide) | 0.16-0.24 | low |
| RG502H | 50:50 poly (D, L-lactide-co-glycolide), acid end capped | 0.16-0.24 | low |
| RG504 | 50:50 poly (D, L-lactide-co-glycolide) | 0.45-0.60 | medium |
| RG505 | 50:50 poly (D, L-lactide-co-glycolide) | 0.61-0.74 | medium |
| RG752S | 75:25 poly (D, L-lactide-co-glycolide) | 0.16-0.24 | low |
| RG755 | 75:25 poly (D, L-lactide-co-glycolide) | 0.50-0.70 | medium |
| RG858S | 85:15 poly (D, L-lactide-co-glycolide) | 1.3-1.7 | medium |

TABLE A-continued

| Trade Name of Commercially Available Polymer (From EVONIK) | Polymer | Intrinsic Viscosity (dL/g) | Molecular Weight (low, medium, high) |
|---|---|---|---|
| R202H | poly (D, L-lactide), acid end capped | 0.16-0.24 | low |
| R203S | poly (D, L-lactide) | 0.25-0.35 | medium |
| R208 | poly (D, L-lactide) | 1.8-2.2 | high |

The biodegradable polymer matrix of the intraocular implant can comprise a mixture of two or more biodegradable polymers. In some embodiments, only one biodegradable polymer listed above is used in the biodegradable polymer matrix. In some embodiments, any one of the biodegradable polymers listed in the above chart can be used in an amount in the range of 12.5% w/w to 70% w/w each in a drug delivery system or implant. In some embodiments, any one of the biodegradable polymers listed in the above chart can be used in an amount in the range of 25% w/w to 50% w/w each in a drug delivery system or implant. In some embodiments, any one of the biodegradable polymers listed in the above chart can be used in an amount in the range of 20% w/w to 40% w/w each in a drug delivery system or implant. In some embodiments, any one of the biodegradable polymers listed in the above chart can be used in an amount of about 15% w/w, about 25% w/w, about 12.5% w/w, about 37.5% w/w, about 40% w/w, about 50% w/w, or about 60% w/w each in a drug delivery system or implant. For example, the implant may comprise a mixture of a first biodegradable polymer and a different second biodegradable polymer. One or more of the biodegradable polymers may have terminal acid groups.

In some embodiments, release of a therapeutic agent from a biodegradable polymer matrix in an intraocular implant can be the consequence of various mechanisms and considerations. Release of the agent can be achieved by erosion of the biodegradable polymer matrix followed by exposure of previously embedded drug particles to the vitreous of an eye receiving the implant, and subsequent dissolution and release of the therapeutic agent. The release kinetics by this form of drug release are different than that through formulations which release agent by polymer swelling alone, such as with hydrogel or methylcellulose. The parameters which may determine the release kinetics include the size of the drug particles, the water solubility of the drug, the ratio of drug to polymer, and the erosion rate of the polymers.

According to some embodiments, compositions and methods extend the brimonidine free base delivery in the vitreous with concomitantly moderate matrix degradation duration. The sustained ocular drug delivery can be achieved by formulating brimonidine free base with properly selected blend of bioerodible poly(D,L-lactide) and/or poly(D,L-lactide-co-glycolide).

According to some example embodiments, a drug delivery system or implant can contain a polymer matrix with an acid-capped poly (D,L-lactide) in an amount in the range of 25% w/w to about 50% w/w. According to some example embodiments, a drug delivery system or implant can contain a polymer matrix with an acid-capped 50:50 poly (D,L-lactide-co-glycolide) in an amount in the range of about 25% w/w to about 50% w/w or about 37.5% to about 50% w/w of the implant. According to some example embodiments, a drug delivery system or implant can contain a polymer matrix with an acid-capped 75:25 poly (D,L-lactide-co-glycolide) in an amount in the range of about 25% w/w to about 50% w/w or about 15% w/w to about 50% w/w of the implant. According to some example embodiments, a drug delivery system or implant can contain a polymer matrix with an acid-capped 85:15 poly (D,L-lactide-co-glycolide) in an amount in the range of about 25% w/w to about 50% w/w or about 30% to about 60% w/w of the implant.

The drug delivery systems are designed to release brimonidine free base at therapeutic levels to the vitreous for a sustained period of time (the brimonidine free base delivery duration), then degrade over period of time in the range of half the brimonidine free base delivery duration to a time equivalent to the brimonidine free base delivery duration. According to other embodiments, the drug delivery system including the polymer matrix can degrade over a period of time of about one quarter the brimonidine free base delivery duration to about one half the brimonidine free base delivery duration. According to other embodiments, the drug delivery system including the polymer matrix can degrade over a period of time of about one third the brimonidine free base delivery duration to about one half the brimonidine free base delivery duration. According to other embodiments, the drug delivery system including the polymer matrix can degrade over a period of time equivalent to about the brimonidine free base delivery duration to about twice the brimonidine free base delivery duration. For example, in an embodiment, an intraocular implant may include a mixture of brimonidine free base and a biodegradable polymer matrix that releases brimonidine free base over a period of time of three months, then the polymer matrix degrades for a period of an additional 2 months until the implant is completely degraded or almost completely degraded. According to some embodiments, the brimonidine free base delivery duration is a period of time in the range of about 1 month to about 6 months, about 1 month to about 5 months, about 1 month to about 3 months, about 1 month to about 4 months, about 2 months to about 4 months, or about 3 months to about 6 months. According to some embodiments, the polymer matrix degradation time for the total drug delivery system is in the range of about 1 month to about 7 months, about 1 month to about 6 months, about 3 months to about 7 months, about 1 month to about 4 months, about 3 months to about 4 months, about 4 months to about 5 months, about 5 months to about 7 months, or about 3 months to about 6 months. According to some embodiments, the polymer matrix degradation time for the drug delivery system is fewer than 10 weeks, fewer than 8 weeks, fewer than 6 weeks, or fewer than 4 weeks.

According to one example embodiment, a biodegradable intraocular implant comprises brimonidine free base associated with a biodegradable polymer matrix, which comprises a mixture of different biodegradable polymers. The brimonidine free base is present in the implant in an amount of 50% by weight, based on the total weight of the implant. A first biodegradable polymer is an acid end capped poly (D,L-lactide) having an inherent viscosity of between 0.16 dL/g and 0.24 dL/g, and comprising 25% by weight of the implant, based on the total weight of the implant. A second biodegradable polymer is a PLGA copolymer having 75 mol % polylactic acid and 25 mol % polyglycolic acid. The PLGA copolymer has an inherent viscosity of between 0.16 dL/g and 0.24 dL/g, and the PLGA copolymer comprises 25% of weight of the implant, based on the total weight of the implant. Such a mixture is effective in releasing an effective amount of the brimonidine free base over a delivery duration of about three months, then degrading the polymer matrix over the span of one-two additional months, less than twice the brimonidine free base delivery duration.

According to another example embodiment, a biodegradable intraocular implant comprises brimonidine free base associated with a biodegradable polymer matrix, which comprises a single type of biodegradable polymer. The brimonidine free base is present in the implant in an amount of 50% by weight, based on the total weight of the implant. In this embodiment, the biodegradable polymer matrix is made of a PLGA copolymer having 85 mol % polylactic acid and 15 mol % polyglycolic acid. The PLGA copolymer has an inherent viscosity of between 1.3 dL/g and 1.7 dL/g, and the PLGA copolymer comprises 50% of weight of the implant, based on the total weight of the implant. Such a mixture is effective in releasing an effective amount of the brimonidine free base over a delivery duration of about three or four months, then degrading the polymer matrix over the span of one-two additional months, less than twice the brimonidine free base delivery duration.

Manufacture of Implants

According to some embodiments, intraocular implants can be formed through suitable polymer processing methods. In an embodiment, a mixture of a therapeutic agent (such as brimonidine free base) may be blended with PLA and/or PLGA polymers in a mixer, such as a Turbula mixer. In an embodiment, the intraocular implants are formed by extrusion. Extrusion can be performed by a suitable extruder, such as a Haake extruder. After the therapeutic agent and the polymer matrix have been blended together, they can then be force fed into an extruder and extruded into filaments. The extruded filaments may then be cut into implants with a target weight. In some embodiments, a 800 µg implant may be cut to deliver about 300 µg, 400 µg, or 500 µg of drug over the brimonidine free base delivery duration. Implants can then be loaded into an injection device, such as a 25G applicator and sterilized. According to some embodiments, the extruded filaments are cut to a weight of less than 1000 µg, less than 800 µg, or less than 600 µg. In some embodiments, the implants can be gamma sterilized. The implants can be gamma sterilized at doses such as 20 kGy to 60kGy, 25 kGy to 50 kGy, 25 kGy to 40 kGy, and the like.

Methods for Treatment

According to an embodiment, a method for treating a posterior ocular condition includes administering an implant, such as the implants disclosed herein, to a posterior segment of an eye of a human or animal patient, and preferably a living human or animal. In some embodiments, a method of treating a patient may include placing the implant directly into the posterior chamber of the eye. In some embodiments, a method of treating a patient may comprise administering an implant to the patient by at least one of intravitreal injection, subconjuctival injection, sub-tenon injections, retrobulbar injection, and suprachoroidal injection.

In at least one embodiment, a method of treating retinitis pigmentosa, glaucoma, macular degeneration, and/or geographic atrophy in a patient comprises administering one or more implants containing brimonidine free base, as disclosed herein, to a patient by at least one of intravitreal injection, subconjuctival injection, sub-tenon injection, retrobulbar injection, and suprachoroidal injection. A syringe apparatus including an appropriately sized needle, for example, a 27 gauge needle or a 30 gauge needle, can be effectively used to inject the composition with the posterior segment of an eye of a human or animal. According to some embodiments, no more than one injection is administered to the patient to treat the condition. According to other embodiments, more than one injection is administered to the patient to treat the condition.

EXAMPLES

Example intraocular implants containing brimonidine tartrate or brimonidine free base and a biodegradable polymer matrix were created and tested for their release and degradation properties. The brimonidine tartrate or brimonidine free base was first weighed and blended with PLA and/or PLGA polymers in a Turbula mixer for 30 minutes. The resulting powder blend was then fed to the Haake extruder by a force feeder. The extruded filaments were cut to implants with a target weight, e.g., 857 µg or 800 µg to deliver 300 µg brimonidine tartrate or 400 µg brimonidine free base per implant. Implants were loaded into 25 G applicators and gamma-sterilized at 25 to 40 kGy dose. The potency per implant was confirmed by a HPLC assay.

Figure 2:
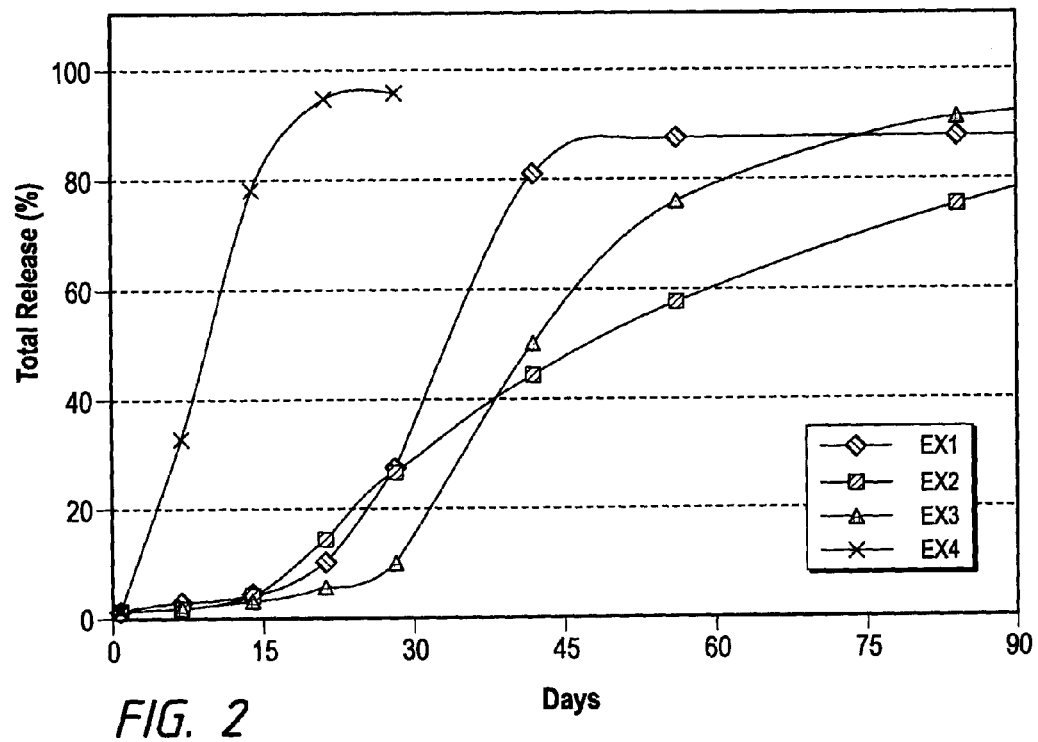
FIG. 2 shows brimonidine free base implant formulation drug release profiles in 0.01 M PBS with a pH of 7.4 at 37 C, according to example formulations.

Examples and Comparative Examples of formulation compositions using brimonidine tartrate (as Comparative Examples 1-4) and brimonidine free base (Examples 1-4) as the drug are shown in Tables B and C, and their drug release profiles are shown in FIGS. 1 and 2, respectively. In FIGS. 1 and 2, the y axis is number of days and the y axis is the percentage (%) of total release. For in vitro drug release testing, four implants per each formulation were randomly cut from extruded filaments, gamma sterilized, and incubated in 10 mL of 0.01M PBS pH 7.4 in a shaking water bath set at 37° C. and 50 rpm. The drug release was sampled at designated time point, and the drug content was analyzed by a HPLC assay. The release medium was completely replaced with fresh medium during each sampling time point. The polymer Mw degradation rate constant k, as determined by incubating implant samples in 0.01M PBS pH 7.4 at 25° C. and their Mw determined by size exclusion chromatography, is included in Tables B and C as well.

TABLE B

Brimonidine tartrate formulation comparative example composition, dimension and degradation kinetic parameters

| Formulation | Brimonidine Tartrate, % w/w | Polymer Excipient, % w/w | | | | | Implant Diameter (µm) | Implant Length (mm) | Implant Weight (µg) | k at 37 C. (1/day), in vitro |
| --- | --- | --- | --- | --- | --- | --- | --- | --- | --- | --- |
| | | R202H | R203S | R208 | RG752S | RG858S | | | | |
| CE 1 | 35 | | 40 | 25 | | | 356 | ~6 | 857 | 0.0041 |
| CE2 | 35 | | 65 | | | | 356 | ~6 | 857 | 0.0033 |
| CE3 | 35 | | 48 | | | 17 | 356 | ~6 | 857 | 0.0073 |
| CE4 | 35 | 15 | 40 | | 10 | | 356 | ~6 | 857 | 0.0064 |

TABLE C

Brimonidine free base example formulation composition, dimension and degradation kinetic parameter

| Formulation | Brimonidine free base, % w/w | Polymer Excipient, % w/w | | | | | Implant Diameter (µm) | Implant Length (mm) | Implant Weight (µg) | k at 37 C. (1/day), in vitro |
| --- | --- | --- | --- | --- | --- | --- | --- | --- | --- | --- |
| | | R202H | RG502H | RG502S | RG752S | RG858S | | | | |
| EX 1 | 50 | | | | 50 | | 356 | ~6 | 800 | 0.02 |
| EX 2 | 50 | | | | | 50 | 356 | ~6 | 800 | 0.012 |
| EX 3 | 50 | 25 | | | 25 | | 356 | ~6 | 800 | 0.012 |
| EX 4 | 50 | | 37.5 | 12.5 | | | 356 | ~6 | 800 | 0.057 |

The polymer matrix degradation was then analyzed both in vitro and in vivo. For in vitro study, the polymer Mw degradation rate constant k as described above was used to calculate the degradation time for the polymer Mw degraded to 1000 Da t(1000) by assuming the degradation follows first order kinetics. For in vivo study, the polymer matrix degradation was determined by harvesting the implant samples that were injected to the vitreous of New Zealand rabbit. The results are summarized in Table D.

TABLE D

Brimonidine formulation in vitro and in vivo drug release and polymer matrix degradation time

| | | In Vitro | | Rabbit | |
|---|---|---|---|---|---|
| Drug Substance | Formulation | Drug Release | Calc. Matrix Degradation t (1000) | Drug Release | Matrix Degradation |
| Brimo Tartrate | CE 1 | 6 months | ~30 months | >6 months | >>6 months |
| | CE 2 | 4 months | ~28 months | 5 months | >>6 months |
| | CE 3 | 4 months | ~15 months | 4.5 months | >>6 months |
| | CE 4 | 3 months | ~14 months | 3 months | >6 month |
| Brimo Free Base | EX 1 | 3 months | ~3 months | ~2 months | 2 months |
| | EX 2 | 4 months | ~7 months | ~3 months | 4 months |
| | EX 3 | 3 months | ~5 months | ~3 months | 3 months |
| | EX 4 | 1 month | ~1 months | ~1 month | 1 month |

In Vitro Testing of Intraocular Implants Containing Brimonidine and a Biodegradable Polymer Matrix Weight Loss Study For the implant weight loss study, each implant was first weighed, moved to a plastic micromesh cassette, and incubated in a glass jar filled with PBS (pH 7.4, 0.01M) before placed in a shaking water bath set at 37° C. and 50 rpm. The implants were harvested at designated time points and dried under vacuum. The weights of the dried implants were recorded and the implant weight loss was calculated. The results are summarized in Table E and show that the brimonidine free base implants lose weight more quickly than those of brimonidine tartrate, implying and illustrating the difference in matrix degradation rate.

TABLE E

Implant weight loss in PBS (pH 7.4, 0.01M) at 37° C.

| Time (wk) | CE 1 | CE 2 | CE 3 | CE 4 | EX 1 | EX 2 | EX 3 | EX 4 |
|---|---|---|---|---|---|---|---|---|
| 1 | 99.7% | 99.7% | 99.7% | 99.5% | 99.4% | 99.5% | 99.7% | 99.3% |
| 2 | 98.8% | 99.4% | 98.9% | 91.7% | 94.2% | 100.7% | 99.0% | 0.0% |
| 4 | 98.5% | 95.5% | 95.7% | 78.7% | 0.0% | 95.0% | 72.2% | |
| 6 | 97.9% | 93.8% | 93.0% | 63.2% | | 81.0% | 0.0% | |
| 8 | 98.8% | 96.6% | 89.3% | 67.0% | | 0.0% | | |
| 10 | 93.1% | 85.7% | 81.5% | 57.3% | | | | |
| 12 | 84.9% | 74.3% | 72.6% | 61.9% | | | | |
| 14 | 84.3% | 40.4% | 72.7% | 67.0% | | | | |
| 16 | 81.2% | 66.9% | 70.2% | 51.5% | | | | |
| 18 | 78.6% | 71.9% | 65.5% | 53.9% | | | | |

Implant Swelling

To investigate the implant swelling, each implant was incubated in 20 mL of PBS (pH 7.4, 0.01M) in a glass scintillation vial and placed in a shaking water bath set at 37° C. and 50 rpm. The implant images were recorded and summarized in FIG. 3. The results show that brimonidine free base implants swelled and degraded much faster than those of brimonidine tartrate.

Figure 4:
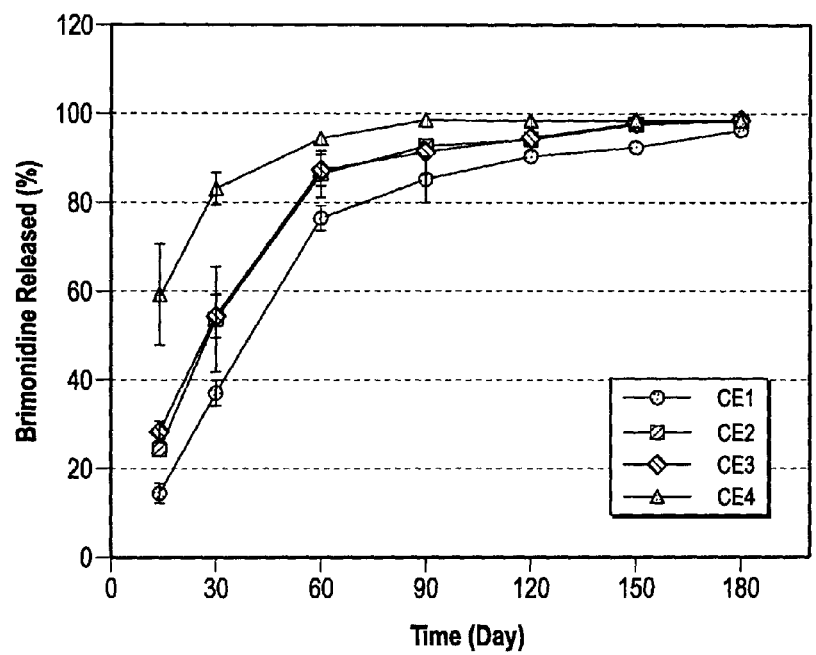
FIG. 4 shows brimonidine tartrate implant formulation drug release profiles in Albino rabbits, according to comparative example formulations.
Figure 5:
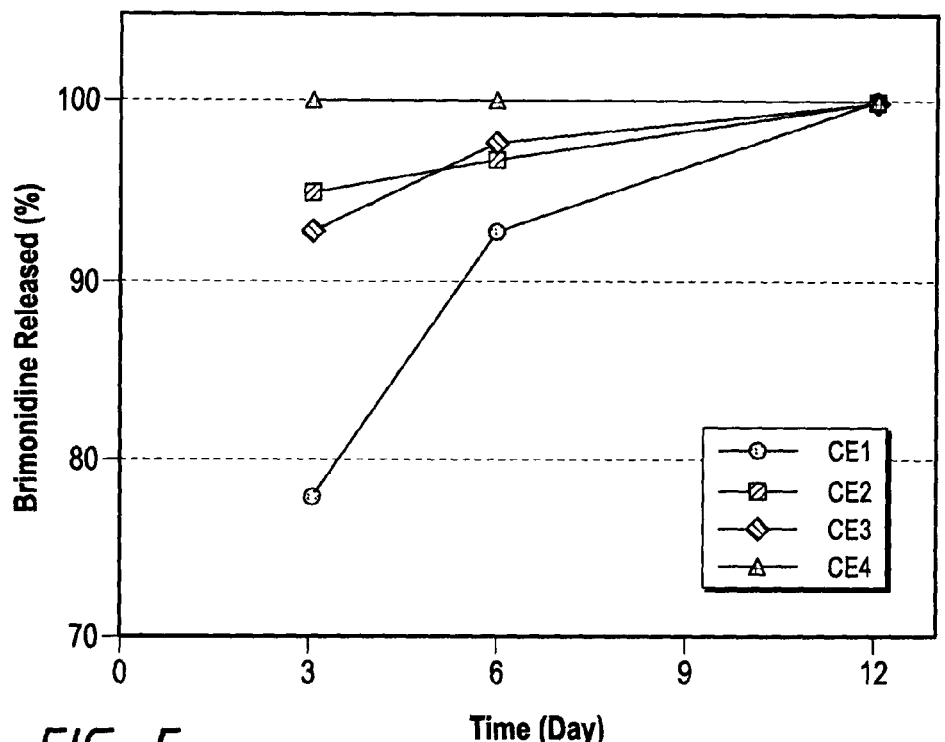
FIG. 5 shows brimonidine tartrate implant formulation drug release profiles in Cyno monkeys, according to comparative example formulations.
Figure 6:
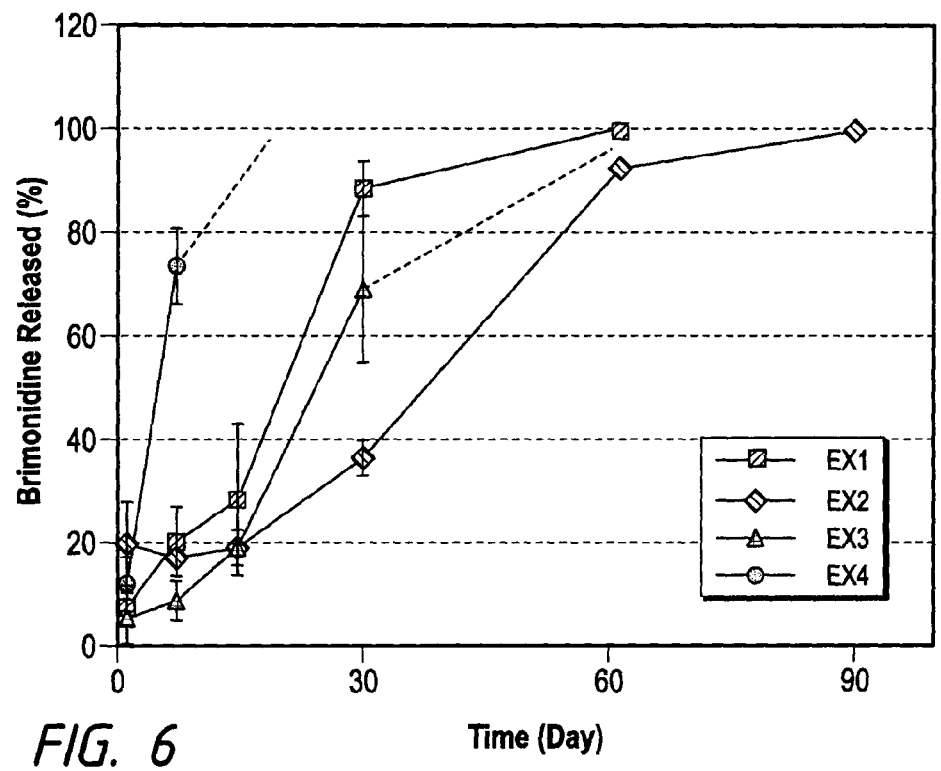
FIG. 6 illustrates brimonidine free base implant formulation drug release profiles in Albino rabbits, according to example formulations.
Figure 7:
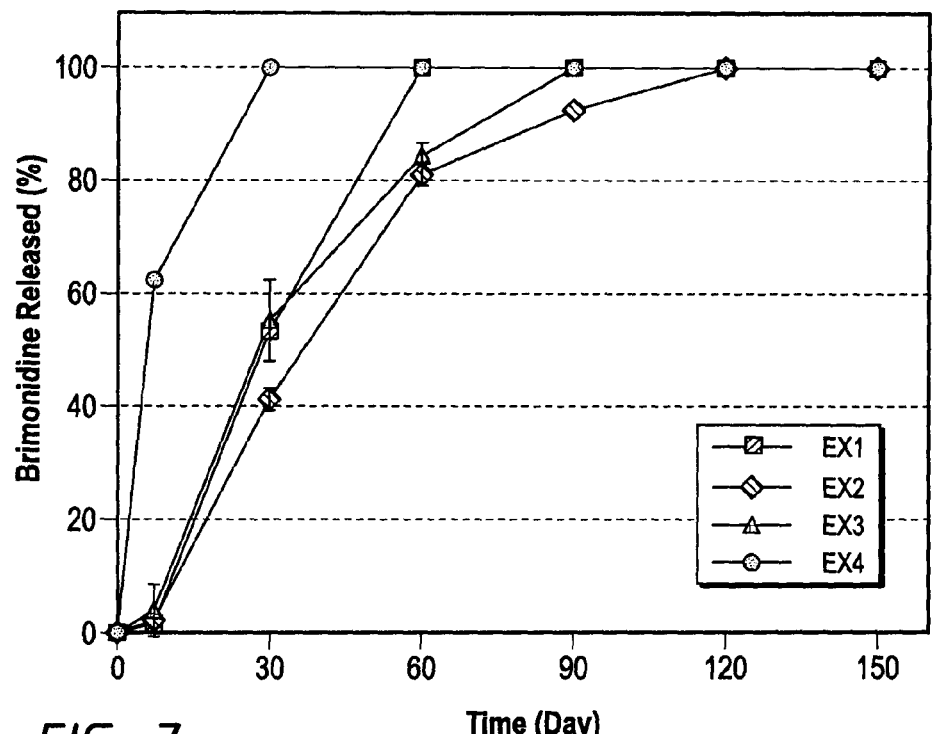
FIG. 7 illustrates brimonidine free base implant formulation drug release profiles in Cyno monkeys, according to example formulations.

In Vivo Testing of Intraocular implants Containing Brimonidine and a Biodegradable Polymer Matrix The drug releases of brimonidine tartrate formulations in rabbit and monkey eyes are shown in FIGS. 4 and 5, respectively. The drug releases of brimonidine free base formulations in rabbit and monkey eyes are shown in FIGS. 6 and 7.

The in vivo drug release profiles were determined by retrieving the implants from the vitreous humor at designated time points. The implant mass was recorded before and after in vivo implantation to determine the quantity of residual polymer matrix. The drug release rates in both animal models showed that Example 4 had the highest release rate, followed by Example 1, then Example 3, then Example 2 demonstrated the slowest drug release rate.

Figure 8:
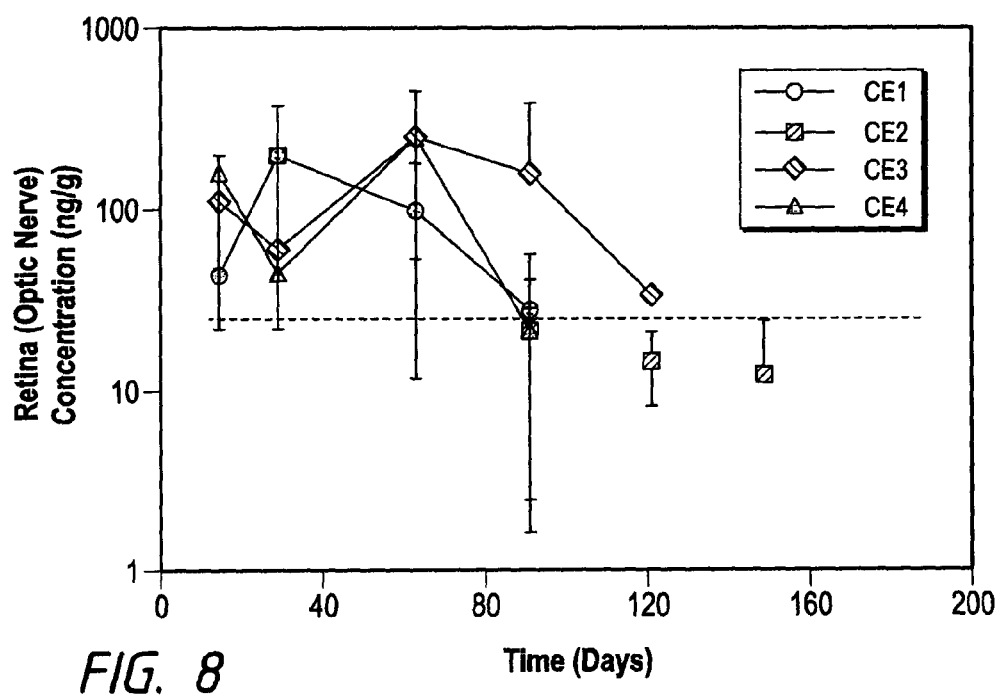
FIG. 8 shows the drug concentration of brimonidine tartrate implant formulations in the retina (optic nerve) of Albino rabbits over time according to comparative example formulations. The dotted line indicates the human α2A EC90 concentration.
Figure 9:
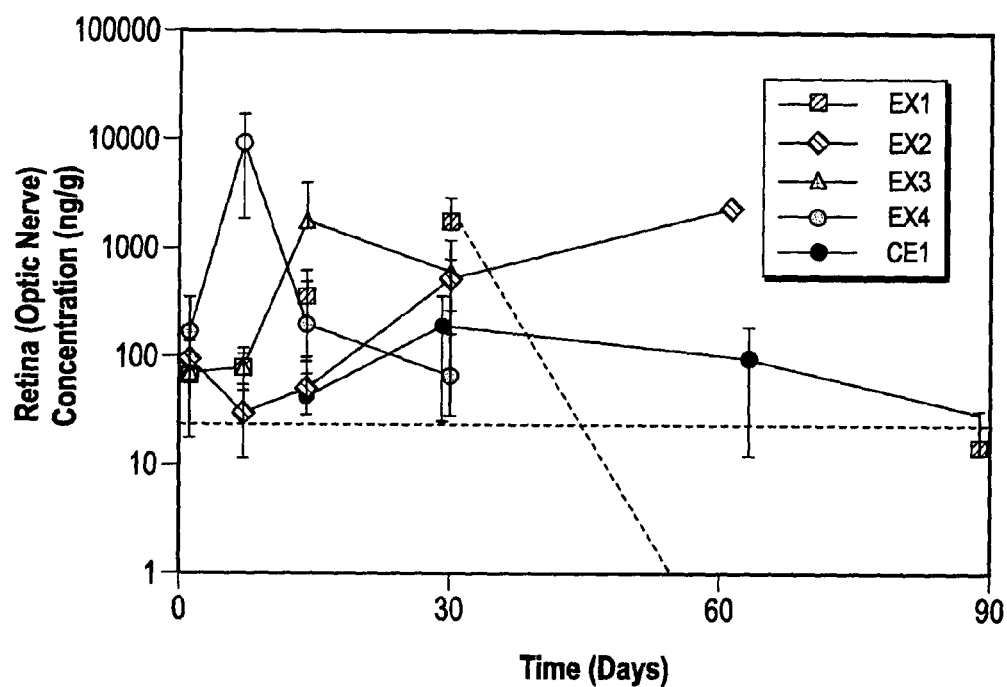
FIG. 9 shows the drug concentration of brimonidine free base implant formulations in the retina (optic nerve) of Albino rabbits over time according to example formulations. The dotted line indicates the human α2A EC90 concentration.
Figure 10:
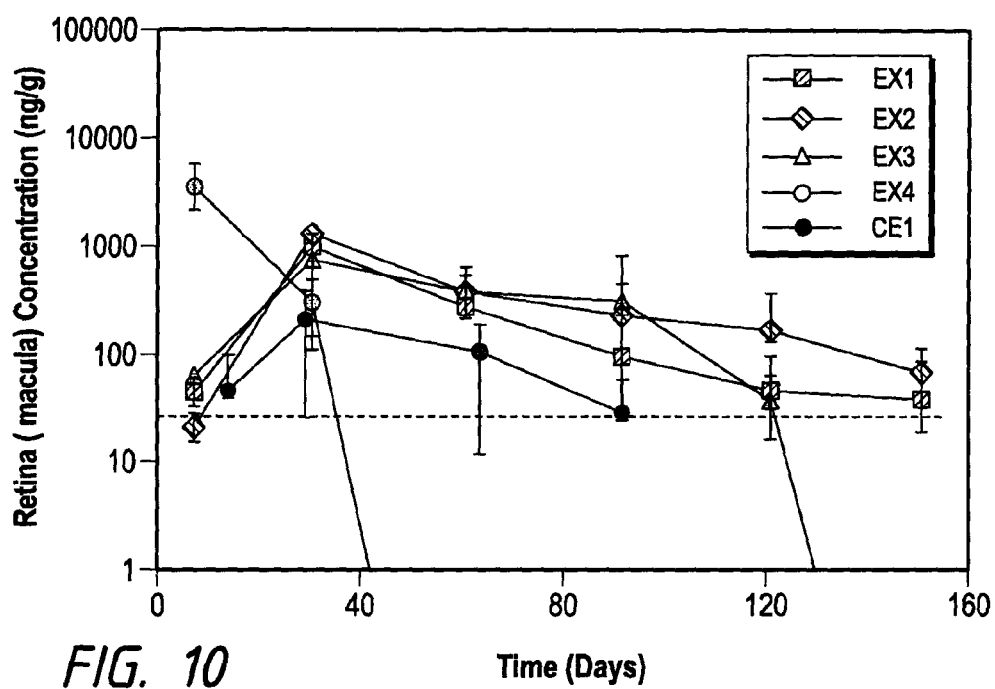
FIG. 10 illustrates the drug concentration of brimonidine free base implant formulations in the retina (macula) of Cyno monkeys over time according to example formulations. The dotted line indicates the human α2A EC90 concentration. For comparison, the CE1 brimonidine formulation is included.

The drug concentration of brimonidine tartrate formulations in the retina (optic nerve) of Albino rabbit eyes are shown in FIG. 8. All formulations maintained the brimonidine concentration above the human α2A EC90 (88 nM, 25.7 ng/mL) for more than 3 months. For brimonidine free base formulations, the drug concentrations in retina (optic nerve in rabbit and macula in monkey) were determined, and the results are shown in FIGS. 9 and 10 for rabbit and monkey, respectively. The period for brimonidine concentration above the human α2A EC90 in the rabbit optic nerve was ≤3 months for all formulations. In a contrast, the time of brimonidine concentration above the human α2A EC90 in the monkey macula was ≥4 months for all formulations except Example 4 that lasted about one month.

Figure 11:
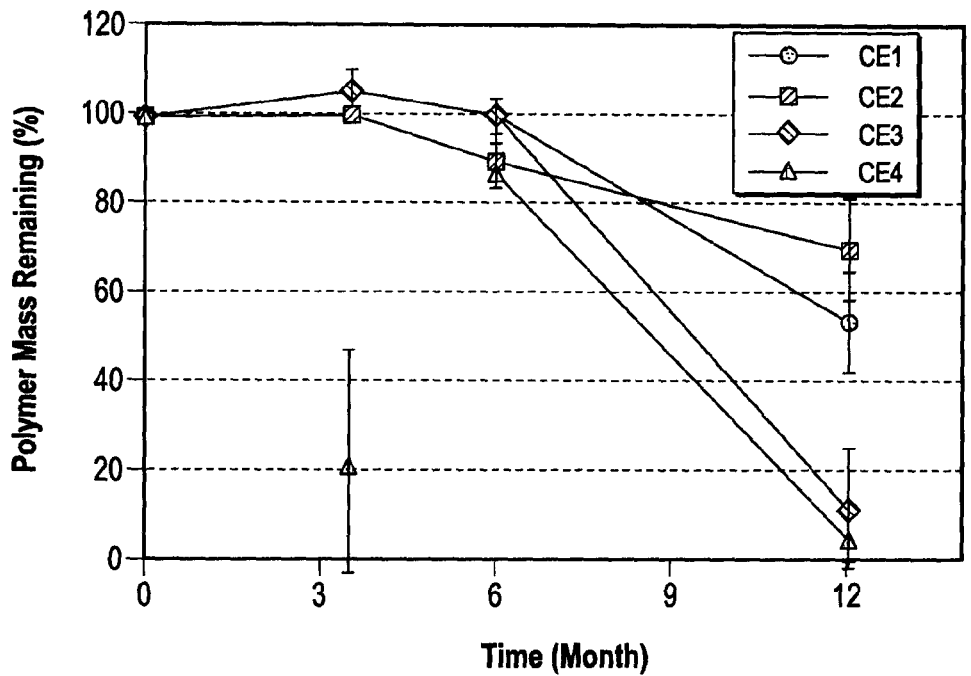
FIG. 11 illustrates the polymer matrix degradation of brimonidine tartrate implant formulations in Cyno monkeys over time, according to comparative example formulations.
Figure 12:
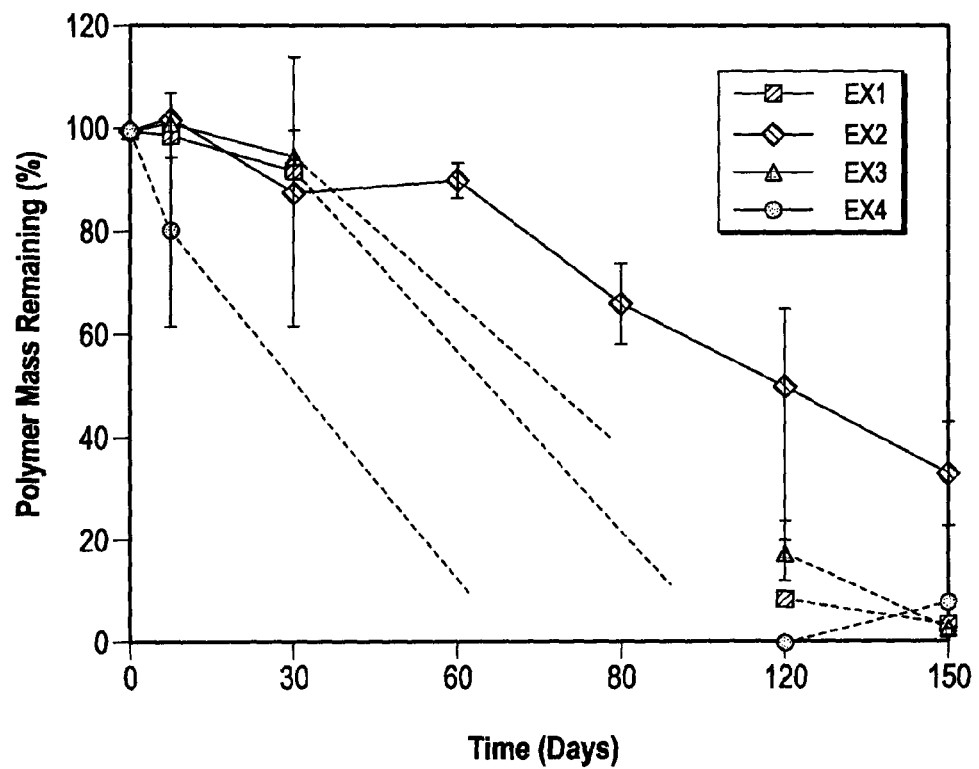
FIG. 12 shows the polymer matrix degradation of brimonidine free base implant formulations in Cyno monkeys over time, according to example formulations.

The polymer matrix degradation of brimonidine tartrate and free base formulations in monkey eyes are shown in FIGS. 11 and 12, respectively. For brimonidine tartrate formulations, less than 50% of matrix was degraded for Comparative Example 1 and Comparative Example 2 formulations in one year, while that for Comparative Example 3 and Comparative Example 4 reached more than 90%. For brimonidine free base formulations, all formulations became small and hard to handle after one month, except Example 2, that the polymer matrix was expected to last for about six months. The in vitro matrix degradation observation matches the in vivo results.

The polymer matrix degradation of brimonidine tartrate and free base formulations in rabbit eyes were analyzed by photo images, and the matrix degradation time is longer than 6 months for brimonidine tartrate formulations and shorter than 4 months for brimonidine free base formulations.

The polymers used in the formulations include, but not limited to, poly(D,L-lactide) and poly(D,L-lactide-co-glycolide). They are summarized in Table A.

The four brimonidine free base formulations demonstrated implants with controlled drug release from one to four months and polymer matrixes lasting for less than two times the drug release duration. In contrast, the brimonidine tartrate formulations delivered the drug for a comparable duration as the brimonidine free base formulations, but the polymer matrix lasted more than two times of the drug release duration.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition while the number of variations of the invention have been shown and described in detail, other modifications, which are within the scope of this invention, will be readily apparent to those of skill in the art based on this disclosure. It is also contemplated that various combinations or subcombinations of the specific features and aspects of the embodiments can be made and still fall within the scope of the invention. Accordingly, it should be understood that various features and aspects of the disclosed embodiments can be combined with, or substituted for, one another in order to perform varying modes of the disclosed invention. Thus, it is intended that the scope of the present invention herein disclosed should not be limited by the particular disclosed embodiments described above, but should be determined only by a fair reading of the claims.

What is claimed is:

1. A solid intraocular implant for the treatment of a posterior ocular condition in a human patient, the solid intraocular implant consisting of:
    a brimonidine free base in an amount of about 40% by weight to about 60% by weight of the implant, based on the total weight of the implant; and
    a biodegradable polymer matrix comprising an acid end-capped poly (D, L-lactide) polymer and a 75:25 poly (D,L-lactide-co-glycolide) polymer;
    wherein the weight ratio of the acid end-capped poly (D, L-lactide) polymer to the 75:25 poly (D,L-lactide-co-glycolide) polymer is 1:1; and
    wherein the implant has a brimonidine free base delivery duration of two months to four months when placed in the eye of a human; and
    wherein the implant has a polymer matrix degradation time in the range of about three months to about six months when placed in the eye of a human.

2. The implant of claim 1, wherein the brimonidine free base is present in an amount of about 50% by weight of the implant, based on the total weight of the implant.

3. The implant of claim 1, wherein the total weight of the implant is about 800 µg.

* * * * *

UNITED STATES PATENT AND TRADEMARK OFFICE
CERTIFICATE OF CORRECTION

PATENT NO. : 9,610,246 B2  
APPLICATION NO. : 14/218324  
DATED : April 4, 2017  
INVENTOR(S) : Jane-Guo Shiah et al.

Page 1 of 5

It is certified that error appears in the above-identified patent and that said Letters Patent is hereby corrected as shown below:

On the Title Page

On the page 3, in Column 2, under "Other Publications", Line 44, delete "LumiganR:" and insert -- Lumigan®: --, therefor.

On the page 3, in Column 2, under "Other Publications", Line 47, delete "Uveites," and insert -- Uveitis, --, therefor.

On the page 3, in Column 2, under "Other Publications", Line 57, delete "Lumigan(R):" and insert -- Lumigan(®): --, therefor.

On the page 3, in Column 2, under "Other Publications", Line 68, delete "Photocoagulatio" and insert -- Photocoagulation --, therefor.

On the page 3, in Column 2, under "Other Publications", Line 70, delete "Beige Ophthalmal," and insert -- Beige Ophtalmol, --, therefor.

On the page 4, in Column 1, under "Other Publications", Line 2, delete "Ophthalmolgica," and insert -- Ophthalmologica, --, therefor.

On the page 4, in Column 1, under "Other Publications", Line 8, delete "Opthalmic" and insert -- Ophthalmic --, therefor.

On the page 4, in Column 1, under "Other Publications", Line 8, delete "Jouranl" and insert -- Journal --, therefor.

On the page 4, in Column 1, under "Other Publications", Line 26, delete "Dexamethason," and insert -- Dexamethasone, --, therefor.

Signed and Sealed this  
Thirteenth Day of June, 2017

Joseph Matal  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 9,610,246 B2

On the page 4, in Column 1, under "Other Publications", Line 37, delete "2-methoxyoestradiol" and insert -- 2-methoxyestradiol --, therefor.

On the page 4, in Column 1, under "Other Publications", Line 37, delete "Angiogeneses" and insert -- Angiogenesis --, therefor.

On the page 4, in Column 1, under "Other Publications", Line 46, delete "Expressior" and insert -- Expression --, therefor.

On the page 4, in Column 1, under "Other Publications", Line 57, delete "Muscosa" and insert -- Mucosa --, therefor.

On the page 4, in Column 1, under "Other Publications", Line 59, delete "Pharamceutical" and insert -- Pharmaceutical --, therefor.

On the page 4, in Column 2, under "Other Publications", Line 6, delete "Dermotol," and insert -- Dermatol, --, therefor.

On the page 4, in Column 2, under "Other Publications", Line 28, delete "Plugof" and insert -- Plug of --, therefor.

On the page 5, in Column 1, under "Other Publications", Line 9, delete "Polyactic" and insert -- Polylactic --, therefor.

On the page 5, in Column 1, under "Other Publications", Line 29, delete "Monocaroxylate" and insert -- Monocarboxylate --, therefor.

On the page 5, in Column 1, under "Other Publications", Line 30, delete "Diabetologica," and insert -- Diabetologia, --, therefor.

On the page 5, in Column 1, under "Other Publications", Line 34, delete "Diabetologica," and insert -- Diabetologia, --, therefor.

On the page 5, in Column 1, under "Other Publications", Line 39, delete "Conjuctiva," and insert -- Conjunctiva, --, therefor.

On the page 5, in Column 1, under "Other Publications", Line 48, delete "5-Fluorouacil," and insert -- 5-Fluorouracil, --, therefor.

On the page 5, in Column 2, under "Other Publications", Line 13, delete "(Polyactates" and insert -- (Polylactates --, therefor.

On the page 5, in Column 2, under "Other Publications", Line 17, delete "Estratopones," and insert -- Estratropones, --, therefor.

On the page 5, in Column 2, under "Other Publications", Line 23, delete "Neuropathis:" and insert -- Neuropathies: --, therefor.

On the page 5, in Column 2, under "Other Publications", Line 30, delete "Transcleral" and insert -- Transscleral --, therefor.

On the page 5, in Column 2, under "Other Publications", Line 55, delete "Antiangionic" and insert -- Antiangiogenic --, therefor.

On the page 6, in Column 1, under "Other Publications", Line 20, delete "Ophthamol." and insert -- Ophthalmol. --, therefor.

On the page 6, in Column 1, under "Other Publications", Line 31, delete "Prostagladin" and insert -- Prostaglandin --, therefor.

On the page 6, in Column 1, under "Other Publications", Line 47, delete "(actide-" and insert -- (lactide- --, therefor.

On the page 6, in Column 1, under "Other Publications", Line 50, delete "Iris-Cillary" and insert -- Iris-Ciliary --, therefor.

On the page 6, in Column 2, under "Other Publications", Line 11, delete "Endsof" and insert -- Ends of --, therefor.

On the page 6, in Column 2, under "Other Publications", Line 17, delete "Alpha-2adrenergic" and insert -- Alpha-2 adrenergic --, therefor.

On the page 6, in Column 2, under "Other Publications", Line 35, delete "(LumiganR):" and insert -- (Lumigan®): --, therefor.

In the Drawings

On sheet 2 of 7, in Figure 3, Line 6, delete "(Disintegraded)" and insert -- (Disintegrated) --, therefor.

On sheet 2 of 7, in Figure 3, Line 7, delete "(Disintegraded)" and insert -- (Disintegrated) --, therefor.

On sheet 2 of 7, in Figure 3, Line 8, delete "(Disintegraded)" and insert -- (Disintegrated) --, therefor.

On sheet 2 of 7, in Figure 3, Line 9, delete "(Disintegraded)" and insert -- (Disintegrated) --, therefor.

In the Specification

In Column 1, Lines 41-42, delete ") quinoxaline)" and insert -- )quinoxaline) --, therefor.

CERTIFICATE OF CORRECTION (continued)
U.S. Pat. No. 9,610,246 B2

In Columns 1-2, Lines 65-67 (Column 1) and Lines 1-2 (Column 2), delete "For example, because of the size of the brimonidine tartrate molecule, the amount of drug that can be loaded into an implant may be limited. Also, the hydrophilic nature of brimonidine tartrate may limit the ability of the drug's use in sustained release formulations." and insert the same on Column 1, Line 64, as a continuation of the same paragraph.

In Column 2, Lines 46-47, delete "37 C," and insert -- 37° C, --, therefor.

In Column 2, Lines 49-50, delete "37 C," and insert -- 37° C, --, therefor.

In Column 2, Line 51, delete "implants" and insert -- implant --, therefor.

In Column 2, Line 52, delete "Formulations" and insert -- formulations --, therefor.

In Column 3, Line 34, delete "that that" and insert -- that --, therefor.

In Column 4, Line 38, delete "mascular" and insert -- macular --, therefor.

In Column 4, Line 39, delete "uvetis;" and insert -- uveitis; --, therefor.

In Column 4, Line 51, delete "opthalmia;" and insert -- ophthalmia; --, therefor.

In Column 5, Line 23, delete "that" and insert -- than --, therefor.

In Column 5, Line 67, delete ") quinoxaline" and insert -- )quinoxaline --, therefor.

In Column 7, Line 56, delete "(D, L-lactide-" and insert -- (D,L-lactide- --, therefor.

In Column 7, Line 58, delete "(D, L-lactide-" and insert -- (D,L-lactide- --, therefor.

In Column 7, Line 59, delete "(D, L-lactide-" and insert -- (D,L-lactide- --, therefor.

In Column 7, Line 60, delete "(D, L-lactide-" and insert -- (D,L-lactide- --, therefor.

In Column 7, Line 62, delete "(D, L-lactide-" and insert -- (D,L-lactide- --, therefor.

In Column 7, Line 64, delete "(D, L-lactide-" and insert -- (D,L-lactide- --, therefor.

In Column 7, Line 65, delete "(D, L-lactide-" and insert -- (D,L-lactide- --, therefor.

In Column 8, Line 7, delete "(D, L-lactide)," and insert -- (D,L-lactide), --, therefor.

In Column 8, Line 9, delete "(D, L-lactide)" and insert -- (D,L-lactide) --, therefor.

In Column 8, Line 10, delete "(D, L-lactide)" and insert -- (D,L-lactide) --, therefor.

CERTIFICATE OF CORRECTION (continued)
U.S. Pat. No. 9,610,246 B2

In Column 10, Line 46, delete "25G" and insert -- 25 G --, therefor.

In Column 10, Line 51, delete "60kGy," and insert -- 60 kGy, --, therefor.

In Column 10, Line 65, delete "subconjuctival" and insert -- subconjunctival --, therefor.

In Column 11, Line 6, delete "subconjuctival" and insert -- subconjunctival --, therefor.

In Columns 11-12, Line 3 (Table B), delete "37 C." and insert -- 37° C. --, therefor.

In Columns 11-12, Line 3 (Table C), delete "37 C." and insert -- 37° C. --, therefor.

In Columns 13-14, Line 14 (Table D), delete "months" and insert -- month --, therefor.

In the Claims

In Column 16, Line 17, in Claim 1, delete "(D, L-" and insert -- (D,L- --, therefor.

In Column 16, Lines 19-20, in Claim 1, delete "(D, L-" and insert -- (D,L- --, therefor.